United States Patent
Vergaro et al.

(10) Patent No.: US 10,902,941 B2
(45) Date of Patent: Jan. 26, 2021

(54) INTERVENTIONAL RADIOLOGY STRUCTURED REPORTING WORKFLOW UTILIZING ANATOMICAL ATLAS

(71) Applicant: EBIT srl, Genoa (IT)

(72) Inventors: Elena Vergaro, Lavagna (IT); Irene Minetti, Molare (IT)

(73) Assignee: EBIT srl, Genoa (IT)

( * ) Notice: Subject to any disclaimer, the term of this patent is extended or adjusted under 35 U.S.C. 154(b) by 526 days.

(21) Appl. No.: 15/697,996

(22) Filed: Sep. 7, 2017

(65) Prior Publication Data
US 2018/0075221 A1 Mar. 15, 2018

(30) Foreign Application Priority Data

Sep. 13, 2016 (EP) ..................................... 16188632

(51) Int. Cl.
| | |
|---|---|
| G16H 15/00 | (2018.01) |
| G06Q 50/24 | (2012.01) |
| G16H 10/60 | (2018.01) |
| G16H 40/20 | (2018.01) |

(52) U.S. Cl.
CPC ............ *G16H 15/00* (2018.01); *G06Q 50/24* (2013.01); *G16H 10/60* (2018.01); *G16H 40/20* (2018.01)

(58) Field of Classification Search
CPC .................................................... G16H 15/00
See application file for complete search history.

(56) References Cited

U.S. PATENT DOCUMENTS

| | | | | |
|---|---|---|---|---|
| 6,213,945 B1* | 4/2001 | Tynan | ...................... | A61B 8/06 600/441 |
| 2005/0273365 A1 | 12/2005 | Baumgartner | | |
| 2007/0198250 A1 | 8/2007 | Mardini | | |
| 2008/0004505 A1* | 1/2008 | Kapit | ..................... | G16H 15/00 600/300 |

(Continued)

FOREIGN PATENT DOCUMENTS

| | | |
|---|---|---|
| EP | 2169577 A1 | 3/2010 |
| EP | 3293651 A1 | 3/2018 |

(Continued)

OTHER PUBLICATIONS

SUITESTENSA CIS Cardiology Information System User Manual, Version 1.9 Nov. 2015.

(Continued)

*Primary Examiner* — John A Pauls
(74) *Attorney, Agent, or Firm* — Gordon & Jacobson, P.C.

(57) ABSTRACT

A computer-implemented method and system are provided for interventional radiology (IR). The method and system store multiple structured reports associated with corresponding IR procedures. Multiple anatomical atlases are stored that correspond to separate vascular districts. The method and system collect IR data corresponding to a select IR procedure and a vascular district of interest and obtain a candidate anatomical atlas from the multiple anatomical atlases based on the IR data. The candidate anatomical atlas illustrates the vascular district model associated with the select IR procedure. The method and system create a structured report based on the collected IR data, the structured report including the candidate anatomical atlas illustrating the vascular district model associated with the select IR procedure.

14 Claims, 25 Drawing Sheets

(56) References Cited

U.S. PATENT DOCUMENTS

| | | |
|---|---|---|
| 2009/0132277 A1 | 5/2009 | Molyneaux |
| 2009/0287487 A1 | 11/2009 | Rossman et al. |
| 2011/0263980 A1 | 10/2011 | Mills et al. |
| 2014/0013199 A1* | 1/2014 | Buurman .............. G06F 19/321 |
| | | 715/226 |
| 2014/0108983 A1 | 4/2014 | Dobkin |
| 2018/0075189 A1 | 3/2018 | Vergaro et al. |

FOREIGN PATENT DOCUMENTS

| | | |
|---|---|---|
| EP | 3293652 A1 | 3/2018 |
| WO | WO2009038585 A1 | 3/2009 |
| WO | WO20120131518 A1 | 10/2012 |
| WO | WO20130179200 A1 | 12/2013 |

OTHER PUBLICATIONS

SUITESTENSA CIS Sistema Informativo de Cardiologia Manuale Utente, Version 2.0 Mar. 2017, in Italian.

English translation of Chapter 12 of SUITESTENSA CIS Sistema Informativo de Cardiologia Manuale Utente, Version 2.0 Mar. 2017.

Search Report dated Jan. 20, 2017, in EP Application No. 16188629.6-1952.

Search Report dated Jan. 25, 2017, in EP Application No. 16188632.0-1952.

* cited by examiner

FIG. 4A

INTERVENTIONAL RADIOLOGY STRUCTURED REPORTING WORKFLOW UTILIZING ANATOMICAL ATLAS

CROSS-REFERENCE TO RELATED APPLICATIONS(S)

The present application claims priority from European Patent Appl. No. EP16188632, filed on Sep. 13, 2016, entitled "INTERVENTIONAL RADIOLOGY STRUCTURED REPORTING WORKFLOW UTILIZING ANATOMICAL ATLAS," herein incorporated by reference in its entirety.

BACKGROUND

Embodiments herein generally relate to interventional radiology, and more particularly to structured reporting workflows within interventional radiology.

Interventional radiology (IR) generally refers to a subspecialty within radiology that affords minimally (or at least limited) invasive diagnosis and treatment of disease. Various equipment is provided to afford image guidance in connection with diagnosis and treatment of disease. A broad range of procedures may be performed in connection with interventional radiology. Non-limiting examples of minimally invasive disease treatment include angioplasty and catheter delivered stents.

A wide range of imaging modalities may be used to afford image guidance, such as x-ray equipment, CT equipment, ultrasound, MRI and other imaging modalities. Interventional radiologist may utilize imaging equipment during a procedure to obtain images that are used in connection with directing interventional instruments through the body. For example, interventional instruments may utilize needles, catheters and the like.

Starting from the preparation of the patient until completion of an interventional radiology procedure, a physician, technician or other medical personnel record various information regarding the patient and procedure into one or more reports to be maintained, such as with the patient's records. Various information systems are used today in connection with generating patient records and reports. For example, radiology information systems (RIS) are utilized in numerous imaging departments and elsewhere within hospitals. The various functions afforded by RIS may include patient scheduling, resource management, examination performance tracking, examination interpretation, results distribution and procedure billing. RIS complement hospital information systems (HIS) and picture archiving and communications systems (PACS) in an effort to afford efficient workflow for radiology practitioners. Another example of an existing information system is a cardiovascular information system (CVIS) which represents an information system uniquely associated with the functionality of catheterization and hemodynamic laboratories. CVIS are configured to collect clinical and procedural data useful to obtain CVIS structured reports. An example commercial CVIS is offered by Ebit S.r.l. of Genoa, Italy, under the tradename Suitestensa. The Suitestensa system is a CVIS PACS imaging and information management software platform that is described more fully at: http://www.esaote.com/en-US/healthcare-it/healthcare-it-software/p/suitestensa-cvis-pacs/ and at: http://www.esaote.com/en-US/healthcare-it/healthcare-it-software/p/suitestensa-ris-pacs/.

However, conventional information systems still experience certain limitations. As one example, the workflow associated with an interventional radiology department exhibits certain unique aspects, whereas no specific data collection tool or information system is provided to facilitate the data collection phase. Instead, today radiologist must compile a "synthetic" report through the use of a conventional radiology information system interface. The conventional RIS interface does not offer a structured data collection capability associated with interventional radiology procedures. In addition, the manner in which conventional RIS interfaces present information to clinicians is not tailored to interventional radiology and consequently offers certain limitations in connection with statistical, clinical and scientific functions.

Therefore, a need remains for improved systems and methods that address the above noted difficulties, as well as other problems that will become available upon reading the text herein.

SUMMARY

In accordance with embodiments herein, methods and systems are described that provide a database structure uniquely associated with interventional radiology that facilitates collection of patient data, clinical data, procedural data as well as information about the materials and therapies, in a structured and graphical manner. The methods and systems facilitate generation of structured reports that are easy to read and include aspects that are automatically derived. The methods and systems provide structured reports that record all data of interest in a manner that is available for statistical and clinical research, as well as for extraction to national registries and the like.

In accordance with embodiments herein a computer system for providing interventional radiology (IR) is provided. The computer system can include a graphical user interface (GUI) and a display. The computer system includes memory to store program instructions and multiple structured reports associated with corresponding IR 1 procedures. The structured reports include sets of data entry sheets, graphical worksheets and text reporting worksheets having a predetermined format and data entry fields uniquely associated with a corresponding aspect of an IR procedure. The memory further stores multiple anatomical atlases that correspond to separate vascular districts. The anatomical atlases include a vascular district model for vascular segments, branches and sub-branches within the corresponding vascular district. The computer system further includes at least one processor that is configured to execute the program instructions to collect IR data through the data entry fields within one or more of the data entry sheets. The IR data corresponds to a select IR procedure and a vascular district of interest. The processor obtains a candidate anatomical atlas from the multiple anatomical atlases based on the IR data. The candidate anatomical atlas illustrates the vascular district model associated with the select IR procedure. The processor further creates a structured report based on the IR data collected. The structured report includes the candidate anatomical atlas illustrating the vascular district model associated with the select IR procedure.

Optionally, the memory may store the anatomical atlases in a library with the anatomical atlases corresponding to separate and distinct vascular districts of interest. At least a first anatomical atlas may include a vascular district model of vascular segments, branches and nodes. The first anatomical atlas may further include a structural model of a portion of a human structural anatomy surrounding the vascular segments. The processor may receive a condition designator indicating a point of interest in a vascular segment of the anatomical atlas. The condition designator may be indicative of a nature of a condition of the vascular segment. The processor may further superimpose a condition indicator on the vascular segment proximate to the point of interest. The condition indicator may be indicative of the condition characteristic. The condition designator may correspond to at least one of a stenosis or aneurysm.

One or more anatomical atlas may be created during a configuration phase and/or during a procedure. A configuration phase may represent any time period before a user is creating a structured report. The configuration phase may simply represent a time at which an anatomical atlas is created, as well as a time at which other aspects of the libraries, catalogues and templates are created.

In accordance with embodiments herein, users may create anatomical atlases from "scratch" during generation of a structured report. For example, the user may use the tools described herein to draw and label any desired branches, vessels, etc., to create a vascular network of interest that is saved as an anatomical atlas.

Optionally, the processor may receive a device designator indicating a point of interest in a vascular segment of the anatomical atlas. The device designator may include a characteristic indicative of a device applied to the vascular segment at the point of interest. The processor may further superimpose a device indicator on the vascular segment at the point of interest. The device indicator may be indicative of the device applied to the vascular segment.

Optionally, the processor may generate a text-based procedure specific (PS) worksheet that includes one or more text reporting regions that are uniquely associated with a corresponding anatomical atlas associated with the local vascular region. The text reporting region may contain a narrative description of the particular IR procedure of interest. The narrative description may comprise a plurality of standardized statements.

Optionally, the processor may generate a text-based procedure specific (PS) worksheet that includes a standardized statement for at least one of a condition, medical device or treatment. The processor may further modify the standardized statement based on a user modification to the anatomical atlas.

The processor may generate a procedure specific worksheet that includes text reporting region. Optionally, the processor may populate the text reporting region with a standardized statement for at least one of a condition, medical device or treatment, receive an input corresponding to a modification to at least one of the anatomical atlas and the text reporting region and update the standardized statement based on the input.

In accordance with embodiments herein, a computer implemented method for providing interventional radiology (IR) is provided. The method comprises storing, in memory, program instructions and multiple structured reports associated with corresponding IR procedures. The structured reports include sets of data entry sheets, graphical worksheets and text reporting worksheets having a predetermined format and data entry fields uniquely associated with a corresponding aspect of an IR procedure. The method stores, in memory, multiple anatomical atlases that correspond to separate vascular districts. The anatomical atlases include a vascular district model for vascular segments, branches and nodes within the corresponding vascular district and presents, on a workstation, data entry sheets that include data entry fields. Further, the method collects IR data, utilizing a graphical user interface (GUI), through the data entry fields within one or more of the data entry sheets. The IR data corresponds to a select IR procedure and a vascular district of interest. The method obtains a candidate anatomical atlas from the multiple anatomical atlases based on the IR data. The candidate anatomical atlas illustrates the vascular district model associated with the select IR procedure and creates a structured report based on the IR data collected. The structured report includes the candidate anatomical atlas illustrating the vascular district model associated with the select IR procedure.

Optionally, the method may store the anatomical atlases in a library with the anatomical atlases corresponding to separate and distinct vascular districts of interest. At least a first anatomical atlas may include a vascular district model of vascular segments, branches and nodes. The first anatomical atlas may further include a structural model of a portion of a human structural anatomy surrounding the vascular segments. The method may receive a condition designator indicating a point of interest in a vascular segment of the anatomical atlas. The condition designator may be indicative of a nature of a condition of the vascular segment. The method may further superimpose a condition indicator on the vascular segment proximate to the point of interest. The condition indicator may be indicative of the condition characteristic (e.g., a lesion characteristic). The condition designator may correspond to at least one of a stenosis or aneurysm.

Optionally, the method receives a device designator indicating a point of interest in a vascular segment of the anatomical atlas. The device designator may include a characteristic indicative of a device applied to the vascular segment at the point of interest. The method may superimpose a device indicator on the vascular segment at the point of interest. The device indicator may be indicative of the device applied to the vascular segment.

Optionally, the method may generate a text-based procedure specific (PS) worksheet that includes one or more text reporting regions that are uniquely associated with a corresponding anatomical atlas associated with the local vascular region. The text reporting region may contain a narrative description of the particular IR procedure of interest. The narrative description may comprise a plurality of standardized statements.

Optionally, the method may generate a text-based procedure specific (PS) worksheet that includes a standardized statement for at least one of a condition, medical device or treatment and may modify the standardized statement based on a user modification to the anatomical atlas.

The method may generate a procedure specific worksheet that includes text reporting region, populate the text reporting region with a standardized statement for at least one of a condition, medical device or treatment and may receive an input corresponding to a modification to at least one of the anatomical atlas and the text reporting region. The method may also update the standardized statement based on the input.

In accordance with embodiments herein, a computer-implemented method is provided for managing interventional radiology (IR). The method receives a procedure designator designating a particular IR procedure from a class of IR procedures, presents one or more data entry sheets associated with interventional radiology (IR). The data entry sheets comprise IR data entry fields concerning IR procedural data and patient data. The data entry sheets are formatted and defined to collect data related to IR. The method collects IR data through the IR data entry fields associated with a patient and the particular IR procedure, automatically identifies a structured report template corresponding to the particular IR procedure based on at least one of the procedure designator or class designator and automatically imports the IR data from the data entry sheets to corresponding fields in the structured report template to create a patient-procedure specific structured report.

Optionally, the structured report template may include a graphical region displaying an anatomical atlas for any vascular district of interest that may designated by at least one of the particular IR procedure or the IR data. The method may further receive a class designator designating a class of procedure that includes one or more candidate procedures in response to the class designator. The method may display a list of candidate procedures that correspond to the class of procedure designated by the class designator. The procedure designator may be selected from the list of candidate procedures. The method may store multiple anatomical atlases corresponding to procedures within the class of procedure, and may select an anatomical atlas from the multiple anatomical atlases. The anatomical atlas selected may correspond to the particular IR procedure and may import the anatomical atlas into the structured report template.

Optionally, the procedure designators designate an angiogram as the particular IR procedure. At least one of the data entry sheets may include an angiogram region that may be configured and formatted to receive information regarding angiograms. The final structured report may include a text reporting region that may contain a narrative description of the particular IR procedure. The narrative description may comprise a plurality of standardized statements. The method may further comprise modifying one or more of the plurality of standardized statements based on the IR data collected through the data entry sheets. The final structured report may include an anatomical atlas corresponding to a non-coronary vascular district associated with the particular IR procedure. The method may further comprise modifying the anatomical atlas. The final structured report may include a text reporting region that may contain a narrative description of the particular IR procedure. The narrative description may comprise a plurality of standardized statements. The method may comprise modifying one or more of the plurality of standardized statements based on the anatomical atlas.

Optionally, the method may further comprise displaying an option list that includes a list of at least one of interventional tools, interventional actions, vascular clinical conditions, or pharmaceutical agents available for use during the IR procedure, and may enter user designation from the option list to the corresponding IR data entry field. The method may store an interventional radiology structured workflow that may include multiple structured report templates associated with particular interventional radiology procedures. The interventional radiology structured workflow may include an anatomical atlas library having multiple anatomical atlases that correspond to separate and distinct vascular districts of interest. The anatomical atlases may be non-patient specific. Optionally, the user may also create an anatomical atlas by drawing the vascular network of interest. The interventional radiology structured workflow may include one or more catalogs containing option lists of at least one of interventional tools, interventional actions, vascular clinical conditions, or pharmaceutical agents available for use during the IR procedure.

In accordance with embodiments herein, a computer system is provided for managing an interventional radiology (IR) The computer system can include a graphical user interface and a display. The computer system includes memory to store program instructions and multiple structured reports associated with corresponding interventional radiology (IR) procedures. The structured reports include sets of data entry sheets having a predetermined format and data entry fields uniquely associated with a corresponding aspect of an IR procedure. The computer system includes at least one processor that is configured to execute the program instructions to receive a procedure designator designating an individual (or particular) IR procedure from a class of IR procedures. The processor collects IR data through the IR data entry fields associated with a patient and the particular IR procedure and automatically identifies a structured report template corresponding to the particular IR procedure based on at least one of the procedure designator or class designator. The processor automatically imports the IR data from the data entry sheets to corresponding fields in the structured report template to create a patient-procedure specific structured report.

Optionally, the structured report template may include a graphical region displaying an anatomical atlas for a non-coronary vascular district of interest that is designated by at least one of the particular IR procedure or the IR data. The processor may receive a class designator designating a class of IR procedure that includes one or more candidate IR procedures. In response to the class designator the processor may display a list of candidate IR procedures that correspond to the class of IR procedure designated by the class designator. The procedure designator may be selected from the list of candidate IR procedures. The memory may further comprise multiple anatomical atlases corresponding to IR procedures within the class of IR procedure. The processor may select an anatomical atlas from the multiple anatomical atlases. The anatomical atlas selected may correspond to the particular IR procedure. The processor may import the anatomical atlas into the structured report template.

Optionally, the final structured report may include a text reporting region that contains a narrative description of the particular IR procedure. The narrative description may comprise a plurality of standardized statements. The processor may be further configured to modify one or more of the plurality of standardized statements based on the IR data collected through the data entry sheets. The final structured report may include a text reporting region that contains a narrative description of the particular IR procedure. The narrative description may comprise a plurality of standardized statements. The processor may be configured to modify one or more of the plurality of standardized statements based on the anatomical atlas. The display may be configured to display an option list that includes a list of at least one of interventional tools, interventional actions, vascular clinical conditions, or pharmaceutical agents available for use during the IR procedure. The processor may be configured to receive a user designation from the option list to the corresponding IR data entry field. The interventional radiology structured workflow, stored in memory, may include one or more catalogs containing option lists of at least one of interventional tools, interventional actions, vascular clinical conditions, or pharmaceutical agents available for use during the IR procedure.

BRIEF DESCRIPTION OF THE DRAWINGS

FIG. 4A illustrates a screenshot of an example data entry sheet that is presented in connection with a specific structured report for which data is to be collected.

DETAILED DESCRIPTION

Figure 1:
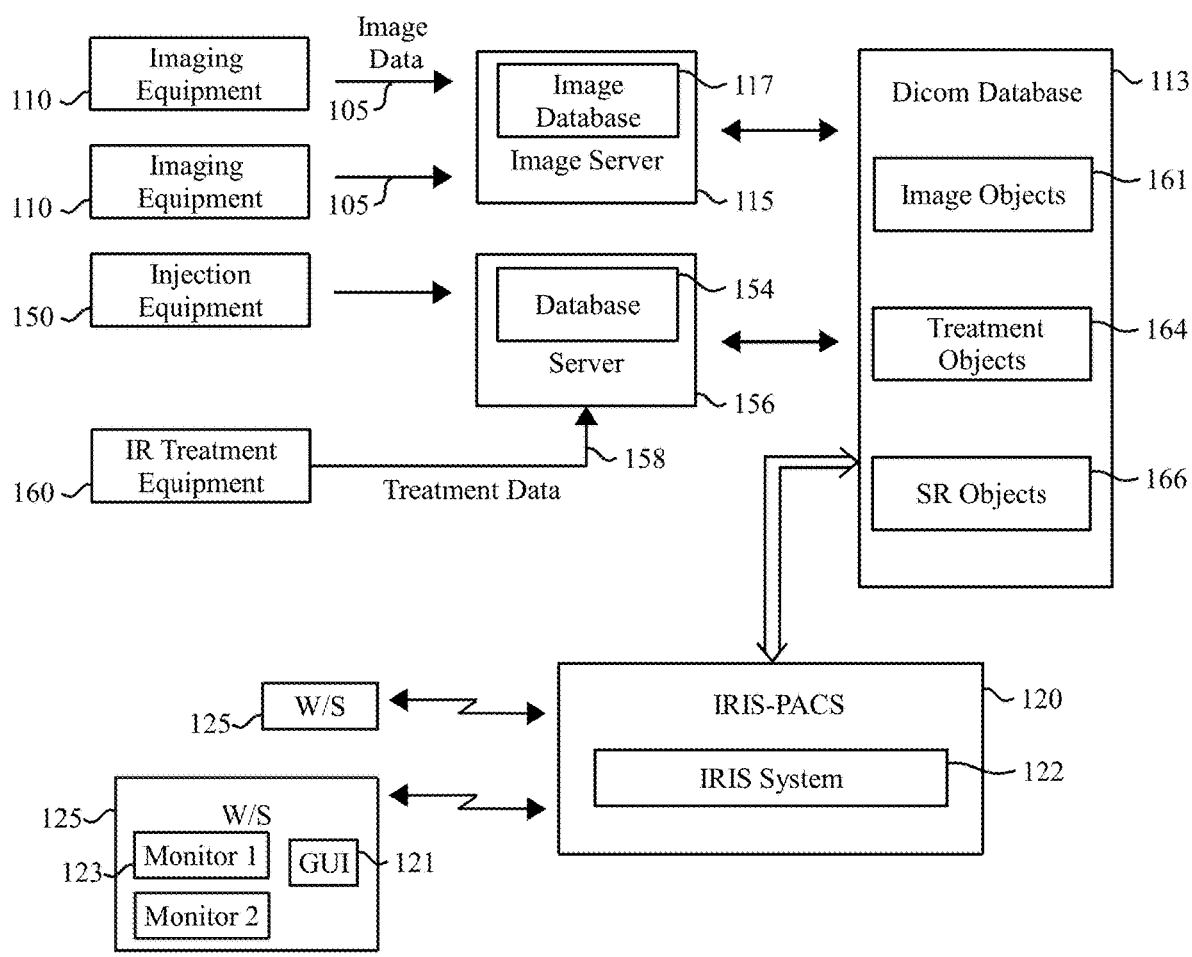
FIG. 1 illustrates a block diagram of an interventional radiology department formed in accordance with embodiments herein.

The embodiments of the systems and methods described herein may be implemented in hardware or software, or a combination of both. However, preferably, these embodiments are implemented in computer programs executing on programmable computer system comprising at least one processor, a data storage system (including volatile and non-volatile memory and/or storage elements), at least one input device, and at least one output device (such as a display). For example and without limitation, the programmable computer system may be a workstation, personal computer, laptop, personal data assistant, and cellular telephone. Program code is applied to input data to perform the functions described herein and generate output information. The output information is applied to one or more output devices, in known fashion.

Each program can be implemented in a high-level procedural or object-oriented programming and/or scripting language for execution on the computer system. However, the programs can be implemented in assembly or machine language, if desired. In any case, the language may be a compiled or interpreted language. Each such computer program is preferably stored on a storage media or a device readable by the computer system, for configuring and operating the computer system when the storage media or device is read by the computer system to perform the procedures described herein. The inventive system may also be considered to be implemented as a computer-readable storage medium, configured with a computer program, where the storage medium so configured causes the computer system to operate in a specific and predefined manner to perform the functions described herein.

The following (as well as additional) acronyms are used throughout:

The vascular system, also called the circulatory system, is made up of the vessels that carry blood and lymph through the body. The arteries and veins carry blood throughout the body, delivering oxygen and nutrients to the body tissues and taking away tissue waste matter. The lymph vessels carry lymphatic fluid (a clear, colorless fluid containing water and blood cells). The lymphatic system helps to protect and maintain the fluid environment of the body by filtering and draining lymph away from each region of the body. The vessels of the blood circulatory system include Arteries (Blood vessels that carry oxygenated blood away from the heart to the body), Veins (Blood vessels that carry blood from the body back into the heart) and Capillaries (Tiny blood vessels between arteries and veins that distribute oxygen-rich blood to the body).

Cerebrovascular system is a term for the blood vessels that carry blood to and from the brain. The arteries (shown in this illustration) are very important since they supply oxygenated blood to the brain.

Peripheral vascular system includes the veins and arteries not in the chest or abdomen (i.e. in the arms, hands, legs and feet). The peripheral arteries supply oxygenated blood to the body, and the peripheral veins lead deoxygenated blood from the capillaries in the extremities back to the heart.

There are various causes of vascular disease. One example is atherosclerosis which is a common cause of vascular disease. Atherosclerosis represents a buildup of plaque, which is a deposit of fatty substances, cholesterol, cellular waste products, calcium, and fibrin in the inner lining of an artery. Atherosclerosis is generally characterized by the accumulation of fatty deposits along the innermost layer of the arteries. If the disease process progresses, plaque formation may take place. This thickening narrows the arteries and can decrease blood flow or completely block the flow of blood to organs and other body tissues and structures.

Another example of vascular disease is an embolus/thrombus, in which a blood vessel may be blocked by an embolus (a tiny mass of debris that moves through the bloodstream) or a thrombus (a blood clot). Another example is inflammation. In general, inflammation of blood vessels is referred to as vasculitis, which includes a range of disorders. Inflammation may lead to narrowing and/or blockage of blood vessels. Another example of vascular disease is trauma/injury in which the blood vessels may lead to inflammation or infection, which can damage the blood vessels and lead to narrowing and/or blockage.

Because the functions of the blood vessels include supplying all organs and tissues of the body with oxygen and nutrients, removal of waste products, fluid balance, and other functions, conditions that affect the vascular system may affect the part(s) of the body supplied by a particular vascular network, such as the coronary arteries of the heart.

One example of vascular disease represents coronary vascular which includes: heart attacks and angina (e.g., chest pains).

There are numerous types of non-coronary vascular disease that concern vascular districts outside of the heart. Examples of non-coronary vascular disease include cerebrovascular disease, peripheral arterial disease, vascular disease of the great vessels, thoracic vascular disease, abdominal vascular disease, peripheral venous disease, lymphatic vascular disease, and vascular diseases of the lungs. Cerebrovascular disease includes: stroke and transient ischemic attack (a sudden or temporary loss of blood flow to an area of the brain, usually lasting less than 5 minutes but not longer than 24 hours, with complete recovery). Peripheral arterial disease includes: claudication (limping because of pain in the thigh, calf, and/or buttocks that occurs when walking), critical limb ischemia (lack of oxygen to the limb/leg at rest). Vascular disease of the great vessels includes: an aortic aneurysm (a bulging, weakened area in the wall of a blood vessel resulting in an abnormal widening or ballooning), coarctation of the aorta (narrowing of the aorta, the largest artery in the body), Takayasu arteritis (a rare inflammatory disease affecting the aorta and its branches). Thoracic vascular disease includes: thoracic aortic aneurysm (a bulging, weakened area in the wall of a blood vessel resulting in an abnormal widening or ballooning in the thoracic, or chest, portion of the aorta). Abdominal vascular disease includes: abdominal aortic aneurysm (a bulging, weakened area in the wall of a blood vessel resulting in an abnormal widening or ballooning in the abdominal portion of the aorta). Peripheral venous disease includes: deep vein thrombosis (also called DVT; a blood clot in a deep vein located within the muscles of the leg), varicose veins and the like. Lymphatic vascular diseases include: Lymphedema (swelling caused by interruption of the normal drainage pattern in the lymph nodes). Vascular diseases of the lungs include: Wegener granulomatosis (an uncommon disease in which the blood vessels are inflamed; mainly affects the respiratory tract and the kidneys), angiitis (inflammation of blood vessels), hypertensive pulmonary vascular disease (high blood pressure in the lungs' blood circulation due to vascular conditions)

FIG. 1 illustrates a block diagram of an interventional radiology department. An interventional radiology department may include multiple rooms in which procedures are performed. The separate rooms may have dedicated systems and equipment installed therein. Additionally or alternatively, portable systems and equipment may be movable between procedure rooms. Various types of systems and equipment may be utilized during any single interventional radiology procedure. In general, radiology procedures involve one or more forms of imaging equipment/systems that afford the physicians the ability to view the region of interest during a procedure. Some types of imaging equipment utilize contrast agents in connection with imaging and as such one or more contrast agent injection systems may be included in the procedure room as well. Procedures also typically utilize various types of interventional equipment that may be used to provide access to the region of interest and/or two enable a treatment to be delivered.

By way of example only, FIG. 1 illustrates an environment that includes one or more interventional radiology imaging equipment 110, one or more injection systems 150 (e.g., contrast agents, etc.) 150, one or more interventional angiography systems 160, and one or more computer processing systems or workstations 125. An interventional radiology information system (IRIS) may be provided as a stand-alone unit or integrated with a picture archive computing system (PACS), together collectively referred to as an IRIS-PACS 120. The IRIS-PACS 120 integrates data and images from numerous imaging equipment 110 modalities (x-ray, CT, NM, MRI, PET, SPECT, ultrasound, etc.). The IRIS-PACS 120 is configured to receive and process images from various types of imaging equipment's, therapy delivery systems, treatment planning systems, and the like. The IRIS-PACS is configured to receive images and other data from multiple healthcare providers, from different departments within a healthcare provider, etc. The IRIS functionality within the IRIS-PACS accesses, stores, updates and manages electronic patient records, and includes one or more modules for generating interventional radiology structured reports and advanced image visualization. The PACS functionality within the IRIS-PACS provides long-term archive and distribution of diagnostic images and patient related data.

Image data 105 is acquired by one or more imaging equipment 110 and stored in an image database 117 on an image server 115. Image data set 105 is then transferred to a DICOM database 113, using a communication protocol, such as one of the DICOM communication protocols. Optionally, the image data sets may be conveyed directly from the imaging equipment 110 to the DICOM database 113. The image data sets may represent two-dimensional images and/or three-dimensional volumetric data sets.

Other data files stored in the DICOM database 113 may include information, referred to as non-image objects, relating to the way in which an image is to be presented. The non-image objects do not include image data but instead include other information related to the image data file(s) to which the non-image objects are to be applied. For example, the DICOM grayscale presentation state (GSPS) object stores the viewing parameters for a DICOM image objects 161 in order to allow for the consistent presentation of the images. A GSPS object may reference more than one image object 161 and, conversely, there may be more than one GSPS object which references a single image object. The DICOM database 113 also stores structured reporting objects 166, as well as other forms of objects and data defined in accordance with the DICOM standard. The data files stored in the DICOM database 113 are often saved into groups, called studies. Each study includes the data files which relate to one particular patient for a particular purpose. One study may include many different types of data files, including image data files such as DICOM Computed Tomography (CT) and Magnetic Resonance Imaging (MR) objects as well as non-image data files such as DICOM GSPS and SR objects.

It should be understood that the systems and modules may be implemented in hardware or software or a combination of both. With respect to the IRIS-PACS 120, modules of the interventional radiology information system 122 are preferably implemented in computer programs executing on programmable computers each comprising at least one processor, a data storage system, and at least one input and at least one output device. Without limitation, the programmable computers may be a server, personal computer, laptop, personal data assistant or cellular telephone. In some embodiments, the IRIS system 122 is installed on the hard drive of the workstation 125, such that the workstation 125 operates with the IRIS-PACS system 120 in a client-server configuration. The IRIS-PACS system 120 and the workstation 125 both include client and server aspects relative to different functions. Optionally, the structure and function of the IRIS-PACS system 120 may be implemented on a stand-alone workstation. In other embodiments, the IRIS system 122 can run from a single dedicated workstation that may be associated directly with a particular imaging equipment 110. In yet other embodiments, the IRIS system 122 can be configured to run remotely on the user workstation 125 while communication with the PACS system occurs via a wide area network (WAN), such as through the internet.

The IRIS-PACS 120 is configured to access the image objects 161 stored in the DICOM database 113 in response to user commands through a computer processing system 125, which can include a processor, display device and input devices (e.g., keyboard, mouse). The DICOM database 113 may represent a core component in many PACS systems. Alternatively, the workstation 125 may be a mobile device or any other suitable access device for displaying image data. Each image object 161 generated from the image data 105 can be expressed in logical parts. One part is known as pixel data that represents the displayed image. The other logical part is the metadata that represents a set of attributes that describes the image such as patient information, study grouping, and image attributes.

The IRIS-PACS 120 provides an interventional radiology structured reporting workflow, in which various aspects of the data entry for the structured report are presented through corresponding windows.

The IRIS system 122 may be provided integrated with a DICOM viewer in order to display the diagnostic images collected during the procedure, or to consult the previous exams. The workstation 125 includes a graphical user interface 121 and displays 123. The displays 123 may include 2 or more monitors. One monitor displays data sheets, worksheets, structured reports and other information as described and illustrated herein. The second monitor displays the corresponding images that are stored in the PACS system and provides a number of tools for visualization and image processing. The foregoing feature is provided by integration between the IRIS and the PACS, so that, by opening a specific procedure in the IRIS, the images—if present—are automatically loaded in the second monitor.

In addition, the IRIS system is configured to open previous images (acquired with the same modality or a different modality, such as XA/XA, or XA/CT, etc.) of the same patient in order to perform a comparison of the clinical status.

Figure 2:
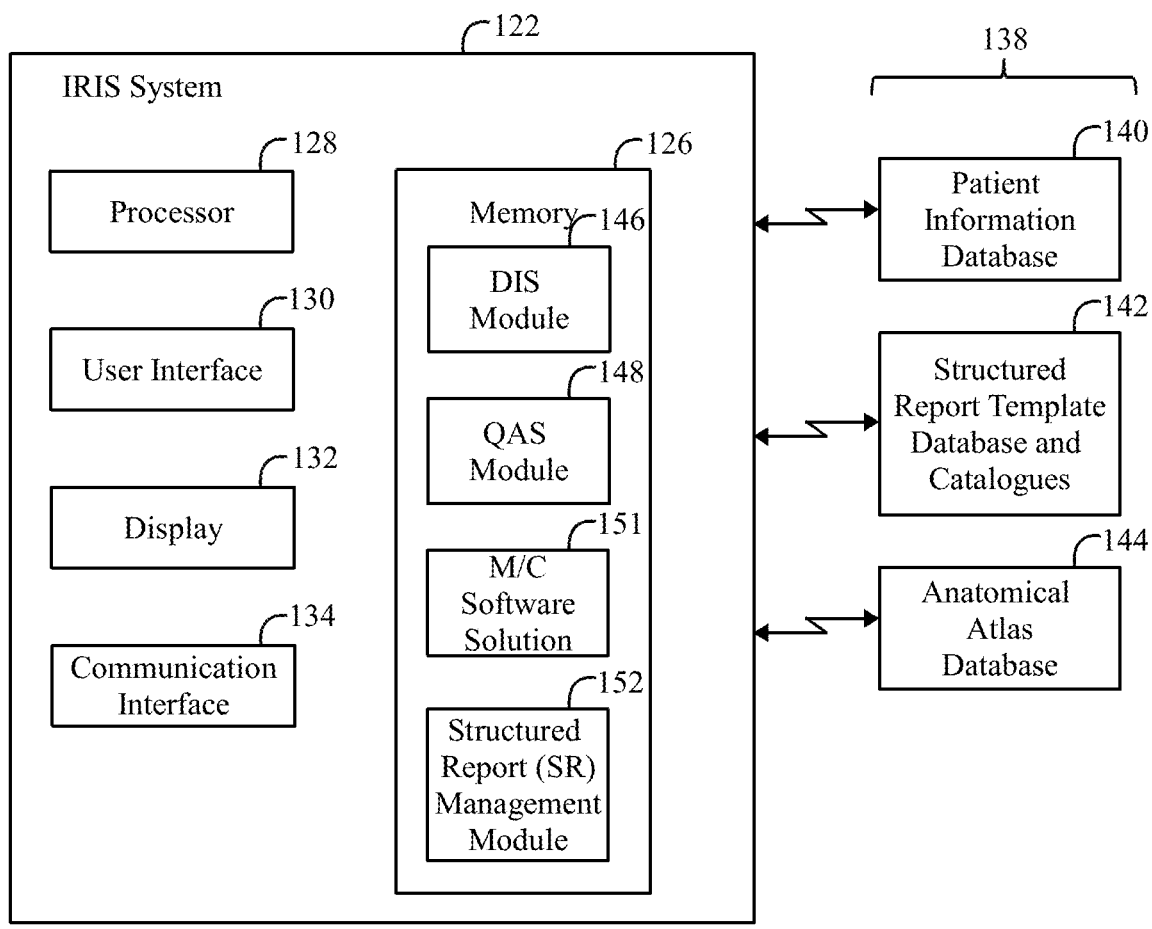
FIG. 2 illustrates an example block diagram of an interventional radiology information system formed in accordance with embodiments herein.

FIG. 2 illustrates an example block diagram of an interventional radiology information (IRIS) system 122 formed in accordance with embodiments herein. The IRIS system 122 is a computer processing system that includes one or more memory 126, one or more processors 128, a user interface 130, a display 132 and one or more communications interfaces 134. The memory 126 includes program instructions directing the one or more processors 128 to perform the operations described herein and implemented one or more software modules discussed herein in connection with managing workflow for structured reporting in connection with interventional radiology.

The IRIS system 122 communicates with one or more servers having memory 138 that store a patient information database 140, a structured report template database 142, and anatomical atlas database 144 and the like. Optionally, the structured report templates and anatomical atlases may be combined into one database. The patient information database 140 includes patient medical records and other information related to individual patients. The structured report template database 142 includes multiple structured report templates associated with corresponding interventional radiology procedures and classes of procedures. For example, each structured report template includes a set of data entry sheets, each of which has a predetermined format and data entry fields uniquely associated with particular aspects of a corresponding procedure and structured report. The anatomical atlas database 144 includes multiple anatomical atlases that correspond to unique portions of the vascular system. The anatomical atlases are not specific to any individual patient, but represent generic templates that may be developed based on models, multiple patients and the like. As one example, anatomical atlases may be developed, referred to as trait specific anatomical atlases, based upon a patient population that exhibits a particular characteristic or characteristics of interest, a disease of interest, demographic of interest, patient history, have undergone a particular past procedure and the like. As explained herein, methods and systems are described that automatically identify a structured report template corresponding to a particular IR procedure based on at least one of the procedure designator (corresponding to the particular IR procedure) and/or a class designator (corresponding to a class of IR procedure).

In the example of FIG. 2, the memory 138 of the servers are described as maintaining the various information as database structures. Optionally, the structured report templates, patient medical records and anatomical atlases may be stored in various formats and upon various medium that may include or not include database structures. The servers and/or memory 138 may be maintained at one or multiple locations, at one or multiple medical facilities, within one or more departments within a medical facility and/or upon one or more pieces of equipment. By way of example, the patient information database 140 may be distributed across multiple physical locations within a medical network or across multiple medical networks. The structured report template database 142 and anatomical atlas database 144 may be maintained upon a single device/workstation or distributed across multiple locations. As one example, a base set of structured report templates and a base set of anatomical atlases may be maintained within memory 126 on the IRIS system 122, while additional structured report templates and anatomical atlases may be maintained elsewhere, within or outside of a medical facility or medical network.

The memory 126 includes, among other things, a diagnostic imaging software module 146 that is configured to provide two-dimensional, three-dimensional and four-dimensional image processing of two-dimensional and volumetric imaging data sets from various modalities (e.g., CT, x-ray, pet, SPECT, ultrasound, MRI, etc.). The memory 126 includes a quantitative analysis software module 148 that is configured to perform quantitative analysis upon diagnostic images, and other patient data. The memory 126 further includes a mobile/cloud software solution 151 that enables clinical collaboration and results distribution over a wide geographic region and to a variety of end computing devices.

The memory 126 also includes an anatomical atlas (AT) management module 152 is configured to manage use of anatomical atlases during report generation. Among other things, the AT management module 152 manages selection and adjustment of vascular segments of interest within anatomical atlases. The AT management module 152 also manages modifications to the anatomical template. For example, the AT management module 152 enables the addition of condition indicators describing (e.g., visually representing) a condition or state of a vascular segment of interest. The AT management module 152 may also enable the addition of device indicators visually representing and/or describing one or more medical devices located within or removed from the vascular segment of interest.

The AT management module 152 receives a class designator designating a class of IR procedure that has been or will be performed. The AT management module 152 also receives a procedure designator designating an individual or particular IR procedure from the class of IR procedure that has been or will be performed. The class designator and procedure designator may be entered in various manners, such as through the graphical user interface of the computer system. Upon receiving the class designator designating the class of IR procedure, the AT management module 152 accesses the procedure/action catalog 318 to obtain one or more candidate IR procedures corresponding to the chosen class. The AT management module 152 displays a list of candidate IR procedures that correspond to the class of IR procedure designated by the class designator. The user may then select a candidate IR procedure from the list of candidate IR procedures, where the chosen candidate IR procedure has a corresponding procedure designator. Thereafter, the AT management module 152 automatically identifies a structured report template corresponding to the particular IR procedure based on at least one of the procedure designator and/or class designator.

The processor 128 provides vendor neutral enterprise archives of patient records and structured reporting results to enable broad compatibility and interoperability of products and technologies, both in connection with DICOM and non-DICOM images.

The communications interface 134 affords access to external resources, such as medical networks, interventional radiology equipment and the like.

Figure 3:
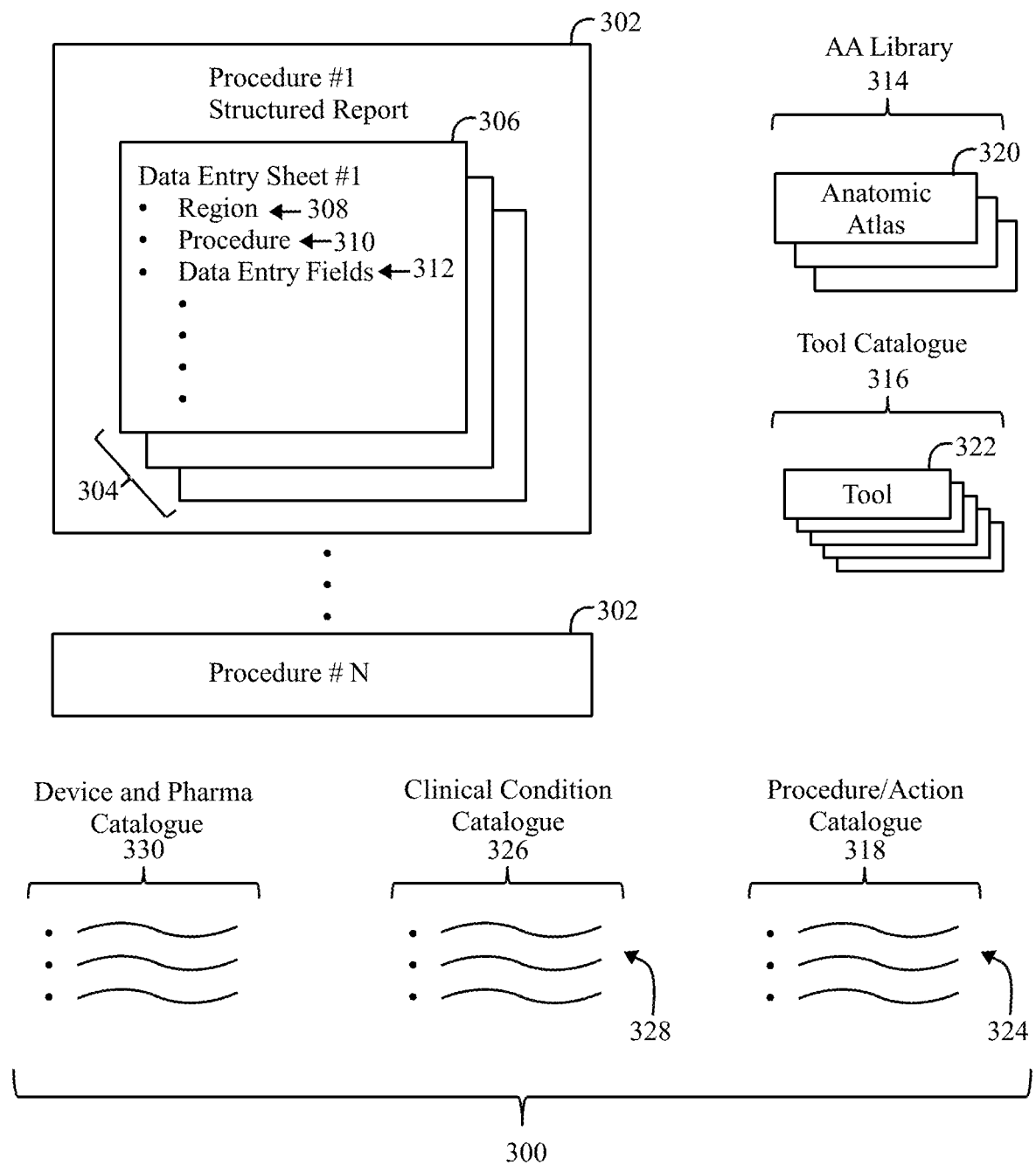
FIG. 3 illustrates an example of at least a portion of the resources utilized in an interventional radiology structured workflow.

FIG. 3 illustrates an example of at least a portion of the resources utilized in an interventional radiology structured (IRS) workflow 300. The IRS workflow 300 includes multiple structured reports 302, each of which is specific to a particular interventional procedure. Each structured report 302 includes a set 304 of data entry sheets 306. Each data entry sheet includes a predetermined format and data entry fields uniquely associated with a particular aspect or aspects of the procedure and structured report. At least one of the data entry sheets 306 includes an anatomical region field 308, a procedure designation field 310, and various other data entry fields 312. The anatomical region field 308 designates the portion of the patient's vascular system, for which the interventional procedure is carried out. The procedure designation field 310 designates the type or nature of the procedure carried out.

The IRS workflow 300 also includes an anatomical atlas library 314, a tool catalog 316, a procedure/action catalog 318, a clinical condition catalogue 326 and a medical device and pharmaceutical catalogue 330. Optionally, the catalogues may be combined or divided in other manners. The anatomical atlas library 314 includes multiple anatomical atlases 320 that correspond to separate and distinct vascular districts of interest. The anatomical atlas library 314 also includes sets of standardized statements to be utilized in connection with generating text reporting regions within structured reports. Each set of standardized statements relates to an individual or particular IR procedure and a vascular district. As explained hereafter, the standardized statements may be formatted in various manners, such as descriptive sentences, that described characteristics such as the condition of a vascular segment, the existence and absence of medical devices, existence and absence of prior treatments and the like associated with particular IR procedure and a vascular district, to which the set of standardized statements relates.

In accordance with at least one embodiment, the standardized statements are phrased as negative or positive statements. For example, the base description for a vascular district or procedure may indicate a normal condition, predetermined abnormal condition, a lack of external medical devices or treatments applied thereto, or the inclusion of predetermined medical devices or treatments and the like. As explained herein, while creating a structured report, the standardized statements are modified to be descriptive of a particular IR procedure and the results of the particular IR procedure. The standardized statements may be automatically populated into a corresponding text reporting region of a worksheet within the structured report. Additionally or alternatively, the standardized statements may be presented as options in a pop-up menu, from which a user may select predefined statements to be added to a text reporting region of a worksheet within the structured report.

While the anatomical atlases 320 correspond to separate and distinct vascular districts of interest, more than one anatomical atlas 320 may at least partially overlap, such as within border regions between adjacent vascular districts. As one example, a template of the supra-aortic vascular district may illustrate at least a portion of the same vascular segments as in a template illustrating a pulmonary vascular segment, greater vessel vascular segment, peripheral vascular segment (e.g., arms, shoulder, upper torso). The anatomical atlases 320 represent general templates and are non-patient specific (e.g., not specific to an anatomy of any individual patient). The tool catalog 316 includes a list of candidate devices/tools 322 that may be utilized in connection with various types of procedures and in connection with different anatomical regions. Examples of devices/tools 322 include stents, medicated stents, endoprosthesis and the like. The procedure/action catalog 318 also includes a list of classes of procedures, with each class of procedure including one or more candidate procedures therein. The procedure/ action catalog 318 includes, for each class of procedure, a list of candidate procedures and/or actions 324 that may be carried out in connection with different interventional procedures. Actions may represent treatments, wherein an example of an action/treatment is to perform RF ablation. The clinical condition catalogue 326 includes a list of candidate clinical conditions 328 (corresponding to condition designators once selected by a user) descriptive of various conditions that may be exhibited by the vascular segment of interest.

The following examples represent nonlimiting examples of classes of potential procedures performed: peripheral vascular, abdominal vascular treatment, thoracic vascular treatment, ablation, angiography, embolisation, percutaneous transluminal angioplasty (PTA). The following examples represent nonlimiting examples of procedures that may be performed: Supra-aortic vessels district: arteriography, supra-aortic vessels district: angioplasty, lower limb district: arteriography, thoracic district: arteriography, abdominal district: arteriography, Abdominal district: angioplasty, Aortic-iliac district: arteriography, aortic-iliac district: angioplasty, femoral-popliteal district: arteriography, femoral-popliteal district: angioplasty. The following examples represent nonlimiting examples of angiograms that may be performed: intrathoracic vessel arteriography, pulmunary artery angiography, Femoral artery angiography, Cerebral arteries angiography, Supra-aortic vessels angiography. The following examples represent nonlimiting examples of arteriography procedures that may be performed: arteriopathy of supra-aortic vessels, cerebral ischemia:asymptomatic stenosis, cerebral ischemia: isolated TIA (Transient Ischemic Attack), cerebral ischemia: crescendo TIA, cerebral ischemia: recurrent TIA, cerebral ischemia: previous stroke, cerebral ischemia: minor stroke, cerebral ischemia: stroke in progress, cerebral ischemia: major stroke, cerebral ischemia: ocular thromboembolism, arteriopathy of lower limbs, arteriopathy of upper limbs.

Examples of the anatomical atlases 320, devices/tools 322 and actions 324 are provided hereafter in connection with a discussion of various embodiments. Embodiments herein map predetermined anatomical atlases 320, tools 322, actions 324, conditions 328 to corresponding structured reports 302 and/or even data entry sheets 306 based on various criteria. As one example, a particular anatomical atlas 320 may be mapped to a particular data entry sheet 306 based on the information entered in the region field 308. As another example, one or more device/tools 322 and actions 324 may be mapped to a particular data entry sheet 306 based on information entered in the procedure field 310.

In accordance with embodiments herein, the data collected may be entered at different times relative to the time in which a procedure occurs. For example, initial information regarding the patient, patient history, past procedures, past prescriptions and the like may be recorded prior to the procedure. Interventional procedure related information may then be entered following the procedure and/or during the procedure.

The IRIS system 122 receives a class designator designating a class of procedure that has been or will be performed. The IRIS system 122 also receives a procedure designator designating a particular IR procedure from the class of IR procedures that has been or will be performed. The class designator and procedure designator may be entered in various manners, such as through a user interface of a workstation. Additionally or alternatively, the class and procedure designators may be recorded in a patient's medical records that are obtained from a medical network or elsewhere. As one example, a window may be presented through the user interface that includes a list of classes of IR procedures, from which the user selects a class (corresponding to a class designator). Upon receiving the class designator designating the class of IR procedures, the IRIS system 122 accesses the procedure/action catalog 318 to obtain one or more candidate IR procedures corresponding to the chosen class. The IRIS system 122 displays a list of candidate IR procedures that correspond to the class of IR procedure designated by the class designator. The user may then select a candidate IR procedure from the list of candidate IR procedures, where the chosen candidate IR procedure has a corresponding procedure designator. Thereafter, the IRIS system 122 automatically identifies a structured report template corresponding to the particular IR procedure based on at least one of the procedure designator and/or class designator.

Figure 4A:
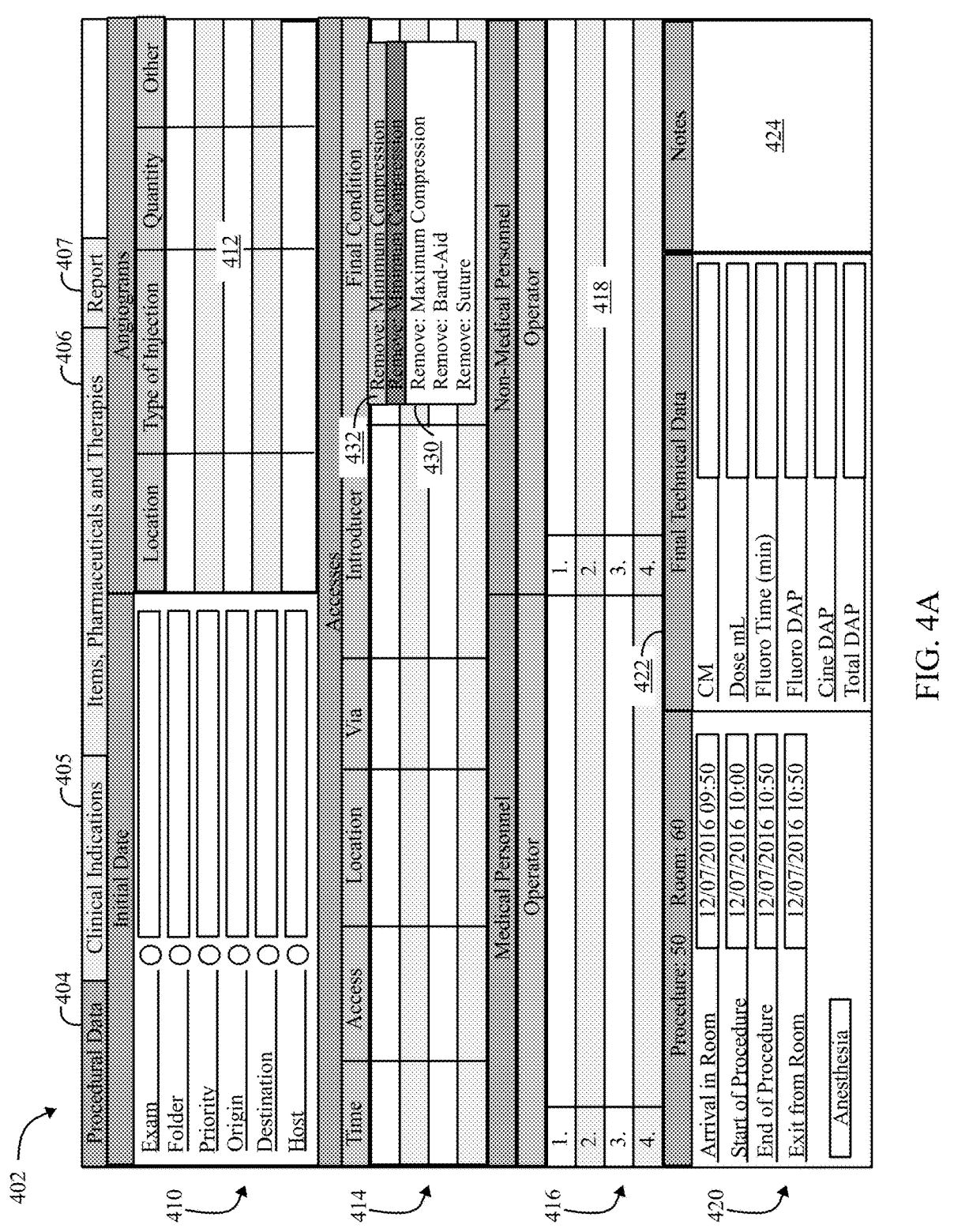

FIG. 4A illustrates a screenshot of an example data entry sheet 402 that is presented in connection with a specific structured report for which data is to be collected. The data entry sheet 402 includes a series of tabs 404-407 that may vary depending upon the particular structured report to be generated. In the example of FIG. 4A, the tabs include a procedural data tab 404, clinical indication tab 405, item—pharmaceuticals—therapies tab 406, and a report tab 407. The procedural data tab 404 may be utilized, among other things, to receive a class designator designating a class of IR procedure to be performed and/or a procedure designator designating a particular IR procedure from the class of IR procedures. The tab 406 is used to collect information about the materials used during the IR procedure (e.g., items such as catheters, stents and so on). The materials may be imported into the report by integration with an external warehouse management system. The tab 406 is also used to collect pharmaceutics dispensed during the procedure and the prescribed therapies pre- and post-IR procedure. The pre-procedure therapy may be optionally imported from previous check-ups registered inside the system. The tabs 404-407 correspond to separate data entry sheets that are formatted and defined to collect data related to an associated IR procedure in a structured reporting format.

FIG. 4A illustrates procedural data entry sheet 402 that is presented in connection with collecting procedural data in accordance with an embodiment herein. When the procedural data tab 404 is selected, the procedural data entry sheet 402 is presented. The procedural data entry sheet 402 includes an initial data region 410, an angiogram region 412, an access region 414, a medical personnel region 416, a non-medical personnel region 418, a procedure region 420, a final technical data region 422 and a notes region 424. It is recognized that additional and/or alternative regions may be presented. For example, the angiogram region 412 may correspond to a different type of procedure, such as an angiography or otherwise.

The initial data region 410 includes fields for entry of information identifying the exam or procedure, such as an examination identifier, procedure folder identifier, priority indicator, origin of department requesting procedure, procedure destination, and host identifier. The angiogram region 412 is configured and formatted to receive information regarding an angiogram performed in connection with the patient, such as the angiogram location, type of injection, contrast agent quantity injected and injection rate, among other things. The angiogram region 412 identifies the types of angiogram that the patient received. The angiogram region 412 may be populated from a drop-down menu of angiogram options (e.g., stored in the action catalog 318 in FIG. 3).

The access region 414 is used to record the nature and manner by which the vascular district of interest is accessed in connection with an interventional procedure. For example, the vasculature may be accessed utilizing an introducer as well as other tools. The access region 414 records location information regarding where an introducer is inserted (e.g., which vein or artery). The type and nature of the introducer is recorded as the manner of access, along with the time at which the introducer was inserted, and a final condition of the access point. The final condition may represent the manner by which the point of insertion is closed following removal of the introducer. Other aspects of the access point may be recorded.

The medical personnel and nonmedical personnel regions 416 and 418 are used to record names/ID of individuals involved in an interventional procedure and optionally their work time within the procedure. The procedure region 420 is used to record time information such as a patient arrival time, procedure start and end times and a time at which the patient exits the procedure room.

The technical data field 422 is used to record imaging equipment dosage and other related information, such as a duration of a fluoroscopy, fluoroscopy dose area product (DAP), radiography DAP, total DAP and the like. For example, when a fluoroscopy is performed during the procedure, the imaging equipment (e.g., fluoroscopy equipment) may record the amount of time during which the patient receives x-rays. The imaging equipment may also record the dosage of the fluoroscopy. Optionally, other dose related information may be recorded in the final technical data field 422.

Optionally, the technical data field 422 may be automatically populated with fluoroscopy duration, dose information and other information. For example, the IRIS system may be directly coupled to one or more of the pieces of equipment outside of or in the interventional procedure room (e.g., the diagnostic equipment, imaging server, DICOM database). The equipment may provide operational information directly to the IRIS system that is automatically populated into the structured report. For example, when a fluoroscopy is utilized during an interventional procedure, the fluoroscopy equipment may be directly coupled to the IRIS system and provide operational information, such as the start and stop times for each fluoroscopic action, the fluoroscopy dose and the like. Other examples of operational information include position and angular orientation of the fluoroscopic equipment relative to a reference point or reference axis (e.g., a reference point or axis on the patient or on the patient bed).

Additionally or alternatively, other types of x-ray equipment may be utilized during an interventional procedure. The x-ray equipment may be directly coupled to the IRIS system to provide operational information.

It is recognized that fluoroscopy and x-ray equipment are non-limiting examples of the type of equipment that may be utilized during an interventional radiologic procedure. Other types of equipment (including non-radiographic equipment) may also be coupled to the IRIS system to automatically provide operational information in connection there with. For example, an ultrasound system may be coupled to the IRIS system to provide operational information.

Optionally, the IRIS system may not be directly coupled to the fluoroscopic, x-ray, non-radiographic, and other equipment. Instead, the operational information for the interventional equipment may be recorded locally on the interventional equipment and/or conveyed to a medical network (e.g., server). The operational information for the interventional equipment, as saved on the interventional equipment and/or medical network, may be accessed by the IRIS system during or following the procedure. For example, when a structured report is being generated (e.g., following a procedure), once basic information concerning the patient and/or particular IR procedure are identified, the IRIS system may access the medical network and automatically download the operational information for the interventional equipment. Additionally or alternatively, an individual preparing the structured report may access the interventional equipment and/or medical network to obtain the operational information and electronically import the operational information to the structured report.

Additionally or alternatively, the IRIS system may prompt the user, when populating the data entry sheet 402, with options to automatically download information from a patient record and/or medical network.

Figure 4B:
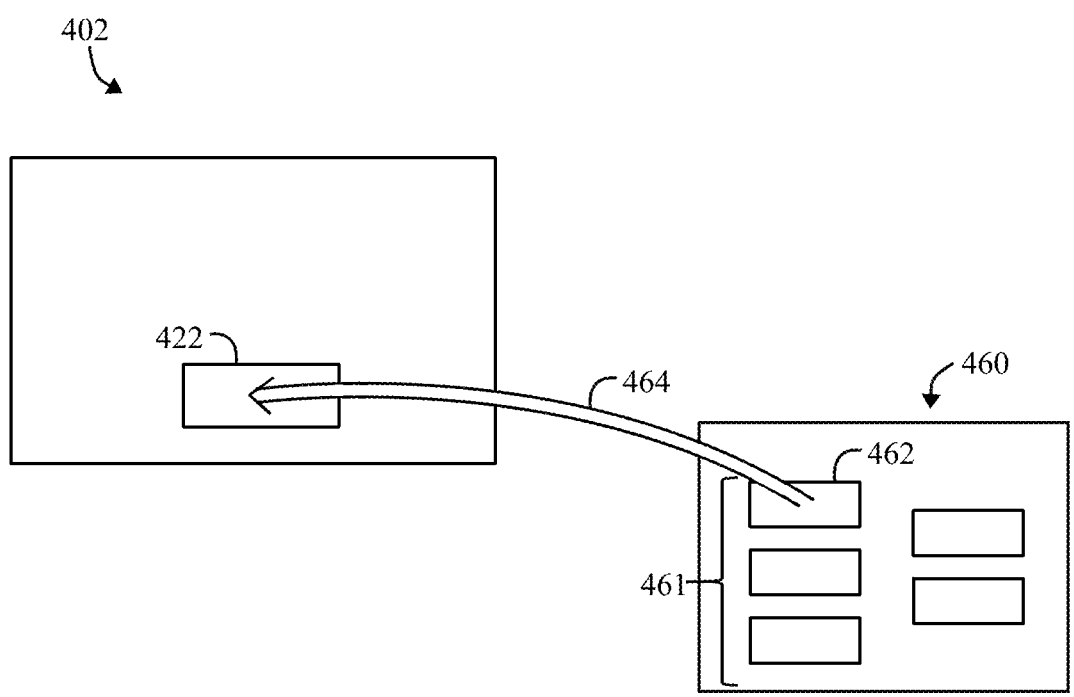
FIG. 4B illustrates a screenshot of an example data entry sheet that is presented in connection with a specific structured report for which data is to be collected.

FIG. 4B illustrates an example of a manner by which interventional procedure related data may be populated semi-automatically within a structured report. In FIG. 4B, the data entry window 402 is presented as part of a graphical user interface on a workstation, while a navigation browser section 460 may be presented on the same or a different workstation. The data entry window 422 includes the various regions discussed in connection with FIG. 4A, including the technical data field 422. Through the navigation browser session 460, the user may navigate to various files and other information organized in various manners. The navigation browser session 460 may be utilized by the user to navigate through the records upon the interventional equipment and/or within a medical network (e.g., server) until locating a particular patient record 461. In the present example, the user may navigate to a server, driver or folder containing the patient record 461 related to a particular patient. The patient record 461 may have various files 462 and information therein, some of which may concern different procedures. For example, different procedures may be performed upon a common individual patient. The different procedures may be performed utilizing the same or different interventional equipment.

The files 462 may contain data corresponding to one or more of the fields within the technical data region 422. The user may select a desired one of the files 462, such as the file corresponding to the operational information for the interventional equipment utilized during a select procedure associated with the structured report. The user may perform a file transfer operation 464 (e.g. receiving a DICOM SR from the equipment) to copy/transfer the file 462 to the technical data region 422. In response to the transfer operation 464, the IRIS system 122 automatically populates the fields within the technical data region 422 with the operational information from the file 462.

Optionally, other mechanisms may be provided to identify one or more files related to the operational information for the interventional equipment, and to transfer files and other information from the medical network and/or interventional equipment. The operational information files may be transferred to the structured report in other manners Returning to FIG. 4A, FIG. 4A also illustrates a drop-down menu 430 that is presented when a user clicks on a corresponding final condition field 432. In the example of FIG. 4A, the final condition field 432 relates to the final condition following the use of an accessory (e.g., in the present example an introducer). When the user desires to record the final congestion resulting from the use of an accessory, the drop-down menu 430 is presented with final condition options that are unique to the final condition field associated with the accessory region 414. By way of example, the options may indicate that, after removal of the introducer, manual compression was applied, a suture was applied, and the like. A list of candidate final condition options is recorded in the action catalog 318 (FIG. 3). The final condition field 432 represents a data entry field 312 to describe a manner (or final status) in which a catheter or other device is removed from a vessel. The corresponding list of condition or status are presented in the final condition field 432 to facilitate selection of predetermined corresponding condition or status associated with the present interventional procedure. Optionally, when the list of actions 324 does not include a corresponding final condition, the user may manually type or speak (utilizing voice recognition software) a desired action.

While not illustrated, it is recognized that menus (e.g., drop-down or otherwise) of predetermined related actions, tools and other information may be presented in connection with each of the regions 410-424 presented in the data entry sheet 402. The corresponding drop-down menus are populated with individual candidate actions, tools and other information based upon the tool catalog 316, action catalog 318 and other prerecorded information.

Figure 4C:
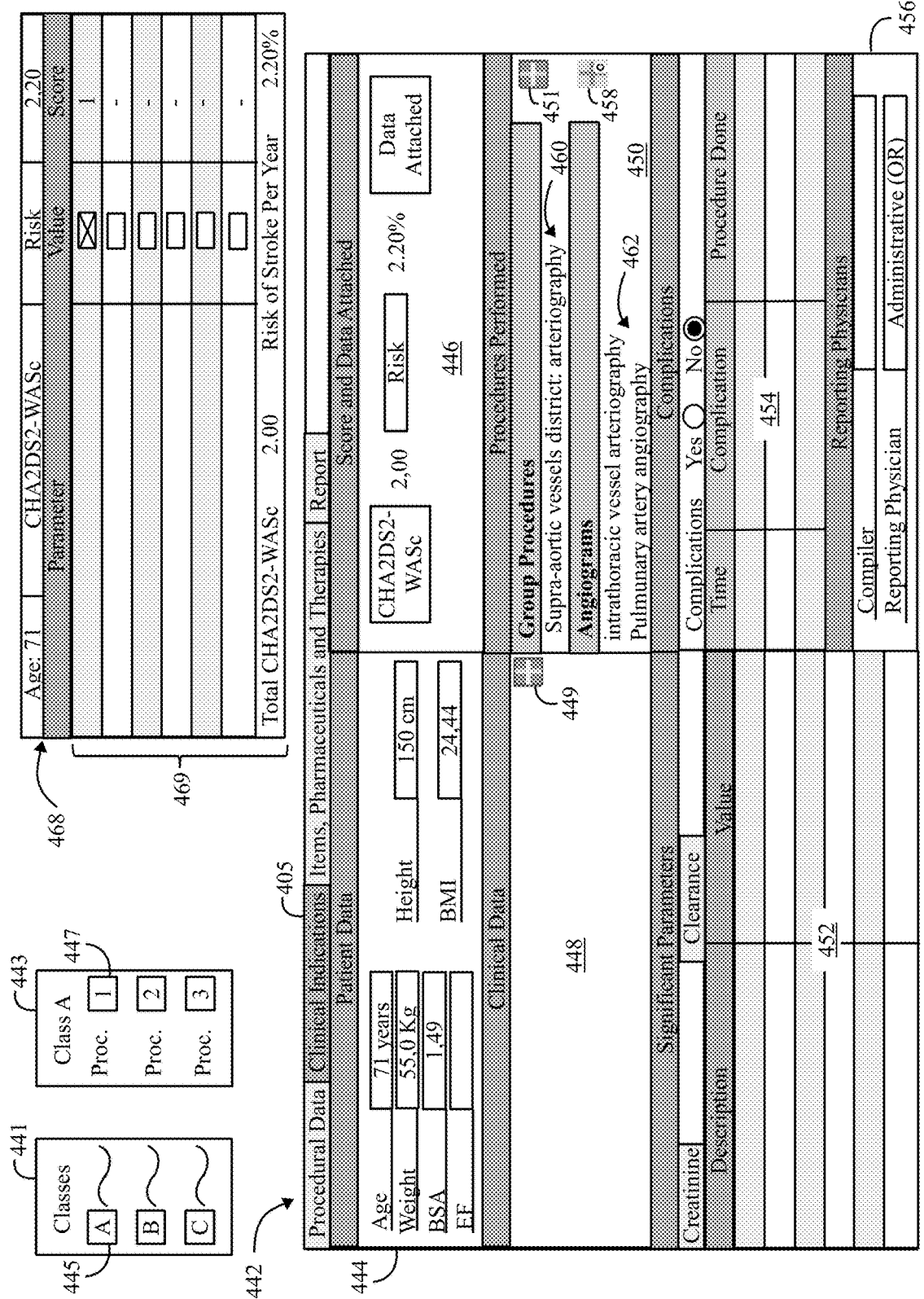
FIG. 4C illustrates a screenshot of an example data entry sheet that is presented in connection with a specific structured report for which data is to be collected.

FIG. 4C illustrates a clinical indication data entry sheet 442 that is presented when the clinical indications tab 405 is selected. The data entry sheet 442 includes a patient data region 444, a score and data attachment region 446, a clinical data region 448, a procedure performance region 450, a significant parameter region 452, a complications region 454, and a reporting physician region 456. Additional and alternative regions may be presented on the data entry sheet 442.

The patient data region 444 is used to enter general patient information, such as age, weight, height and the like. The patient information is then automatically used by the IRIS system to calculate other parameters such as the body surface area (BSA), body mass index (BMI) and cardiac ejection fraction (EF) and the like. Additionally or alternatively, the BSA, BMI and/or EF may be manually inserted and/or received from another system. Optionally, when the user hovers the mouse over the BSA, BMI or EF fields, the corresponding formula may be presented in a pop-up window. Within the pop-up window, the user may adjust the parameter values and/or the formula utilized to calculate the corresponding parameter.

The score and data attachment region 446 is used to form a patient score and to attach related data. The scores may be preconfigured in connection with particular interventional radiology procedures. For example, FIG. 4C illustrates an example of a score window 468 that may be presented when a particular score is selected within the score and data region 446. The score window 468 illustrates a list of parameters 469 that may be utilized as a basis to derive a score associated with an individual patient, as well as parameters there are used to determine a risk factor associated with the patient. In the present example, the window 468 lists the parameters 469 such as whether the patient is a female, experiences insufficient cardiac output, hypertension, is diabetic and the like. A score is associated with each parameter, which is then combined (e.g., sound). A risk calculation is then applied indicating a risk that the patient may experience a stroke.

The present example illustrates scoring associated with a risk of stroke. It is understood that alternative types of scores and risks associated with other physiologic characteristics may be utilized. Various scores may be calculated associated with interventional procedures.

Figure 4D:
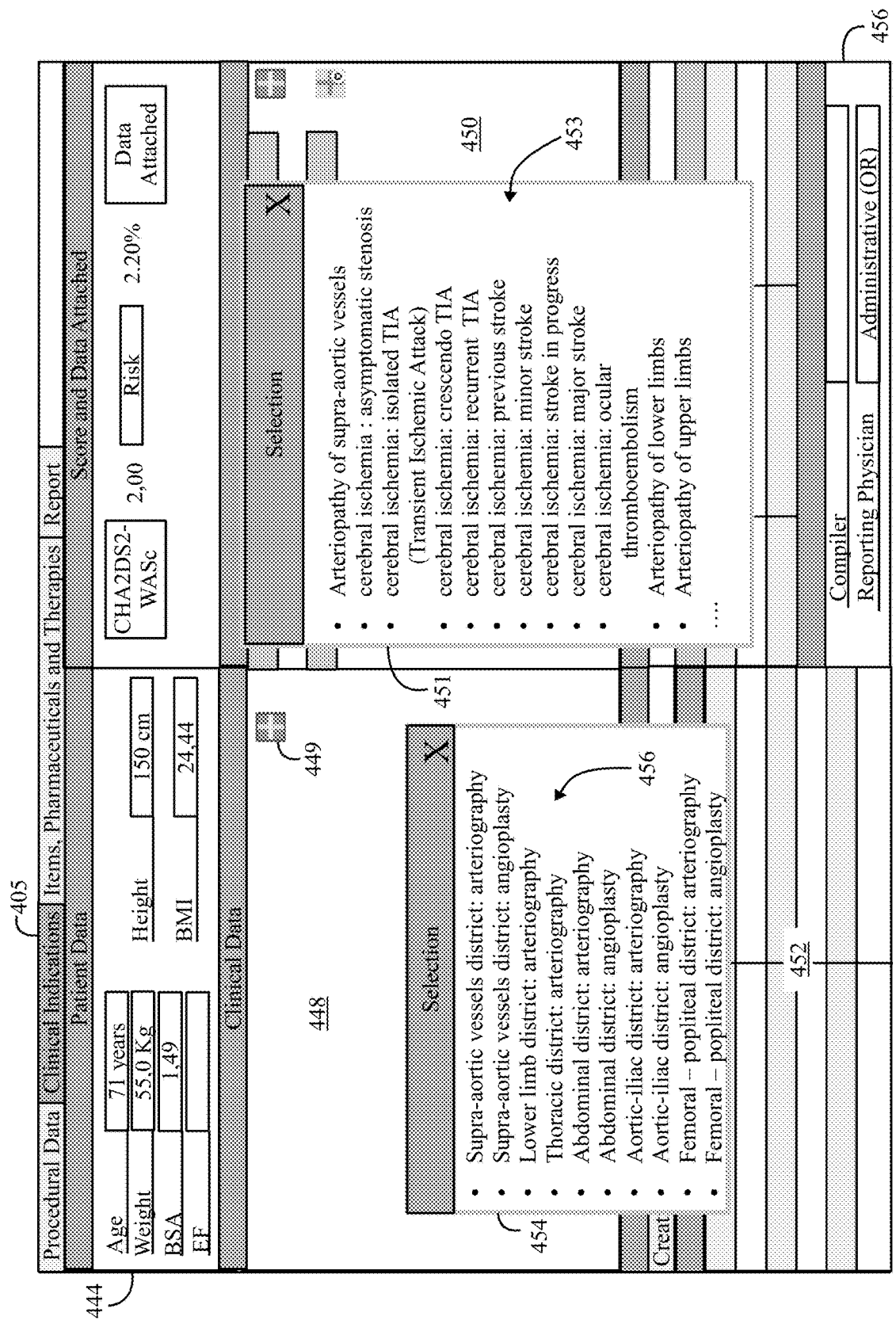
FIG. 4D illustrates a screenshot of an example data entry sheet that is presented in connection with a specific structured report for which data is to be collected.

The clinical data region 448 is used to record clinical data. The clinical data region 448 may be utilized to insert information regarding past illnesses and other information. For example, the user may select an add icon 449 (FIG. 4C). In response to the selection of icon 449, the IRIS system presents a window 451 (FIG. 4D) including a list of clinical conditions 453. The conditions 453 may be organized into categories that may be expanded and collapsed. In the example of FIG. 4D, the conditions may be organized based on vascular districts of the patient. For a particular vascular district, a list of subcategories may be presented, where the subcategories maybe based on a nature or severity of a condition (e.g., cerebral ischemia—minor stroke; cerebral ischemia—stroke in progress; cerebral ischemia—major stroke).

The procedures region 450 is used to record details regarding particular IR procedures performed upon the patient. The procedures region 450 includes an add icon 451 that facilitates entry of particular IR procedures. When the icon 451 is selected, the IRIS system presents a window 454 (FIG. 4D) that includes a list of candidate IR procedures 456 that may be performed during interventional radiology. The candidate IR procedures 456 may indicate both the nature of the procedure (angioplasty, arteriography) and the location (aorta, abdominal, chest) at which the IR procedure is to be performed. The list of candidate IR procedures 456 may be obtained from the procedure/action catalog 318 (FIG. 3). The candidate IR procedures within the procedure/action catalog 318 may be tailored to individual countries, regions or otherwise. In addition, the candidate IR procedures may be tailored based on individual insurance and healthcare coding regulations. When a particular candidate IR procedure 456 is selected, the corresponding insurance reimbursement code may be recorded.

The significant parameters region 452 is used to record parameters that are considered significant to the IR procedure and/or patient, providing a description and a value for the parameter. Optionally, a drop-down menu may be presented with examples of descriptions associated with significant parameters. Examples of parameters of interest include pressure values, hemoglobin, INR (International Normalized Ratio).

The complications region 454 is used to describe any complications experienced during the IR procedure, as well as the time at which the complication occurred, the nature of the complication and the phase of the IR procedure in which the complication occurred. Examples of complications of interest include local complications like infection or general complications like a stroke, pneumotorace, TIA, Heart Failure, etc. The reporting physician region 456 is used to record the names of the reporting physician or other individuals entering data in the structured report.

FIG. 4C also illustrates a class of procedure window 441 that may present a list of classes of IR procedures, from which the user may select. Based on the selection for a class of IR procedure (corresponding to a class designator 445), a procedure window 443 may be presented with a list of individual IR procedures corresponding to the class of IR procedures chosen from window 441. The classes of IR procedures and individual IR procedures illustrated in the windows 441 and 443 have corresponding class designators 445 and procedure designators 447 correspond to the classes and individual IR procedures stored in the catalog 318. While the windows 441 and 443 are illustrated in FIG. 4C, it is recognized that the windows 441 and 443 may be presented at any time independent of and separate from the other data sheet and information illustrated in FIG. 4C.

Figure 4E:
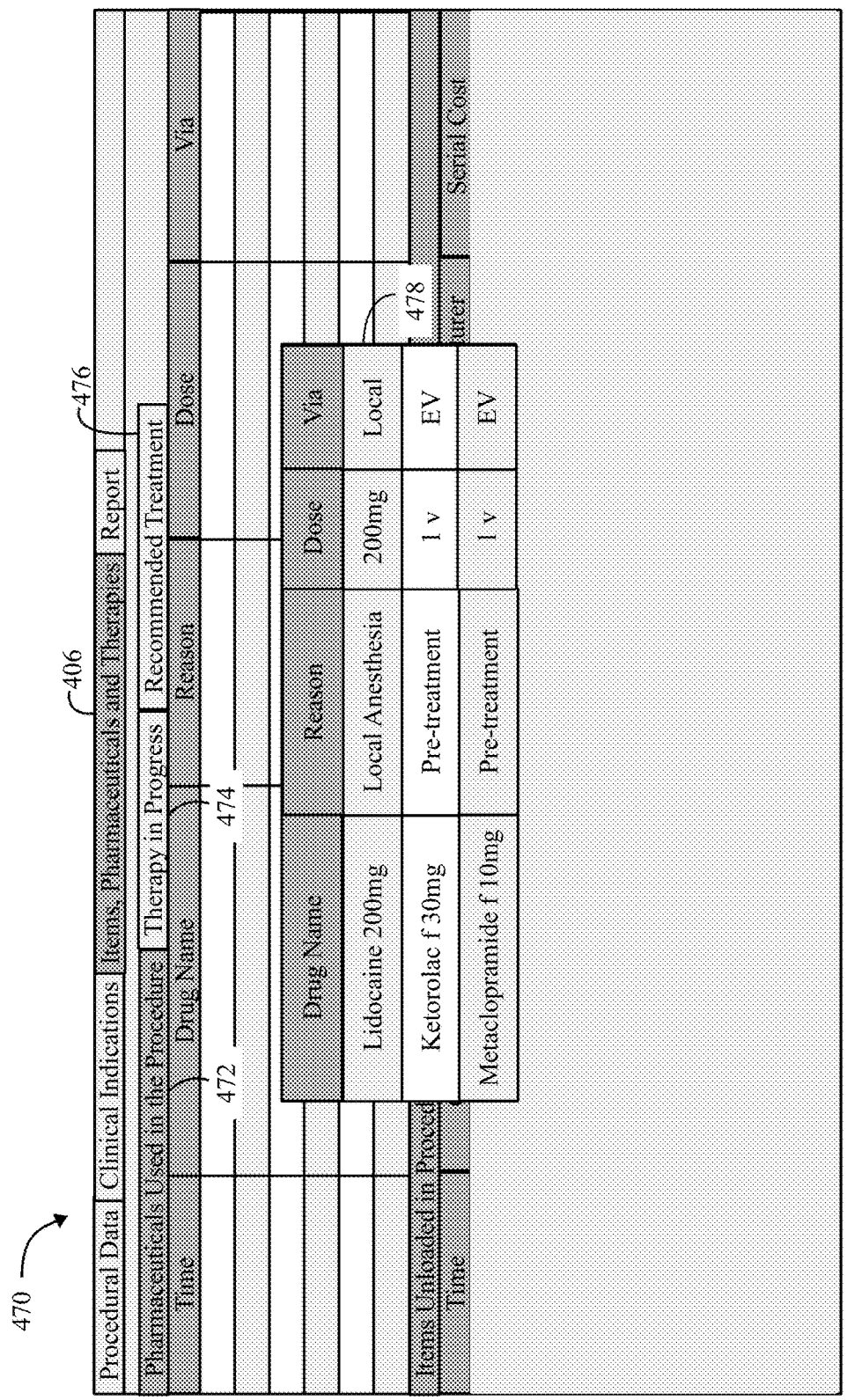
FIG. 4E illustrates a screenshot of an example data entry sheet that is presented in connection with a specific structured report for which data is to be collected.

FIG. 4E illustrates an example of an items and pharmaceuticals data entry sheet 470 that may be utilized to enter information concerning pharmaceuticals and other items used during a procedure. When the tab 406 is selected, the data entry sheet 470 is presented, including sub options for entering pharmaceuticals used in an IR procedure 472, therapies in progress 474 and recommended treatments 476. When the pharmaceuticals used tab 472 is selected, the user is afforded the option to enter a time at which a drug is delivered, the drug name, the reason for administering the drug, the dose and the manner in which the drug was administered. Additional or alternative fields may be offered. When the user selects a particular field, optionally, a drop-down menu may be presented, such as window 478. The window 478 may present various options from a corresponding catalog (e.g., pharmaceuticals catalog 330 in FIG. 3).

It is recognized that the foregoing examples are nonlimiting examples of the types of windows that may be presented. Alternative formats, positions and presentations may be utilized. Optionally, the IRIS system may present windows with a list of options for the reason for administering the drug, the dose and the manner in which the drug is delivered.

In accordance with embodiments herein, once all or a portion of the procedural data, clinical indications and items and pharmaceuticals have been entered, the IRIS system generates one or more procedure specific reports. When the user desires the IRIS system to generate procedure specific reports, the user may select the generate report icon 458 (FIG. 4A). In response thereto, the IRIS system generates a procedure specific report in connection with each procedure identified in the procedures region 450.

Figure 5A:
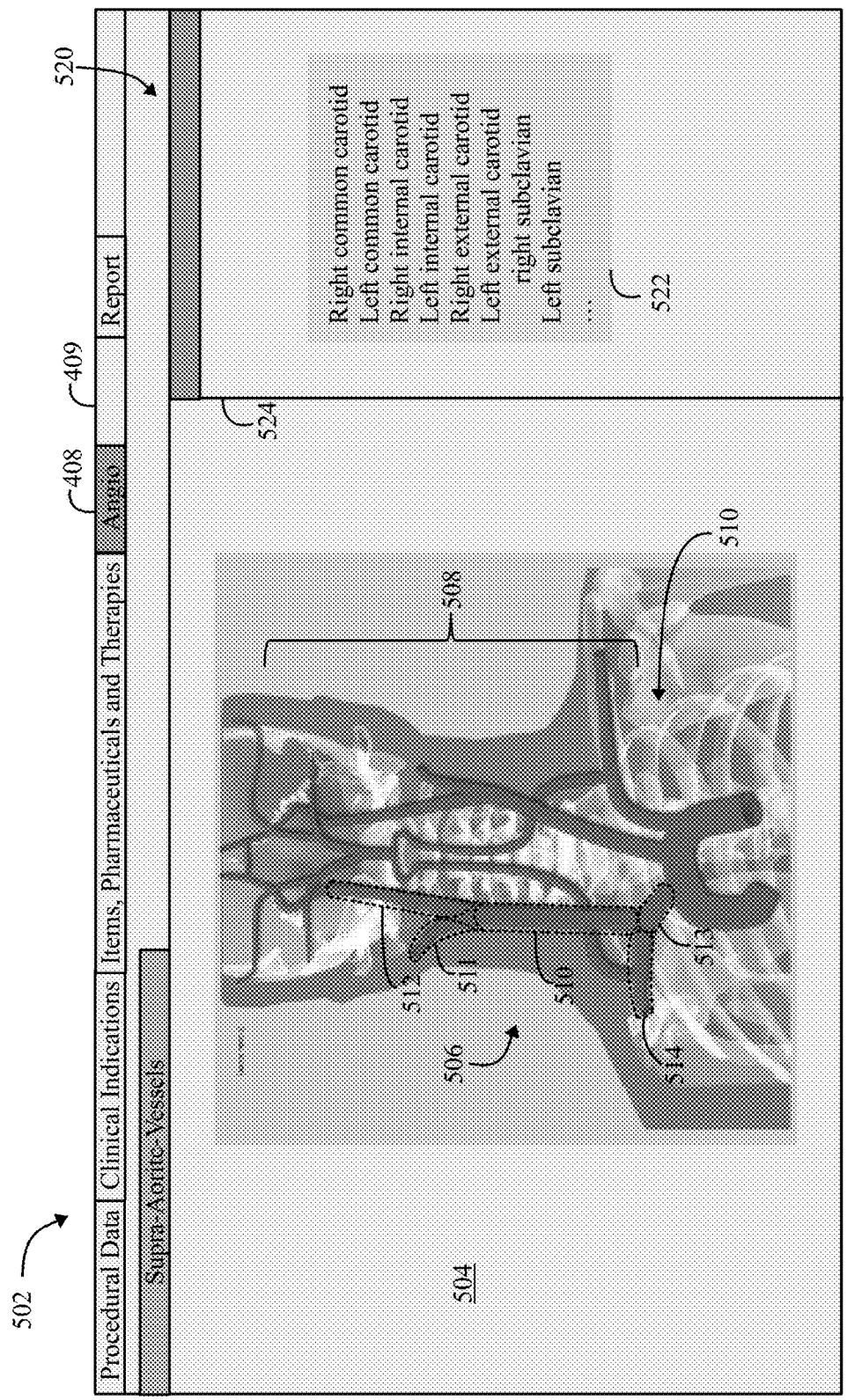
FIG. 5A illustrates an example of a procedure specific worksheet formed in accordance with an embodiment herein.

In the present example, an angiography (ANGIO) of supra-aortic vessels procedure 460 and percutaneous transluminal angioplasty (PTA) procedure 462 were identified in connection with FIGS. 4A-4E. Accordingly, the IRIS system generates an ANGIO report and a PTA report designated by the report tabs 408 and 409, respectively (as designated in FIG. 5A). In FIG. 5A, the ANGIO procedure 408 is selected. Accordingly, the worksheet 502 illustrates an anatomical atlas 506 that corresponds to the supra-aortic vessel district.

FIG. 5A illustrates an example of a graphical procedure specific (PS) worksheet 502 (graphics based) within a patient-procedure specific structured report formed in accordance with an embodiment herein. The graphical PS worksheet 502 includes a graphical reporting region 504 that presents an anatomical atlas 506 associated with a local vascular region in which the procedure or procedures have been or will be performed. The anatomical atlas 506 includes a vascular district model 508 of vascular segments, branches, nodes and the like. The vascular segments form a vascular network. In the present example, the vascular district model 508 corresponds to supra-aortic vessels. The anatomical atlas 506 may also include a structural model 510 of a portion of the human structural anatomy surrounding the vascular segments, such as muscle, bone, ligaments, nerves, tissue within the local region. In the present example, the structural model 510 illustrates a portion of the upper torso (shoulders, ribs, spine), the neck and a portion of the skull. Additionally or alternatively, the structural model 510 may illustrate muscles, ligaments, nerves, tissue, organs and the like.

The anatomical atlas 506 is obtained from the anatomical atlas library 314 (FIG. 3). The AA library 314 retains various anatomical atlases associated with different local vascular districts. Optionally, the AA library 314 may include more than one anatomical atlas for a particular local vascular district, where the anatomical atlases may differ slightly from one another. For example, posterior and anterior anatomical atlases may be presented for a common local vascular district, but from different perspectives. Optionally, more than one anatomical atlas may be provided for a single local vascular district based upon the type of procedure to be performed.

The anatomical atlas 506 is divided into vascular segments, each of which is labelled. Examples of the vascular segments 510-514 are illustrated in dashed lines. The user designates one or more vascular segments 510-514 through a user interface. For simplicity, only a portion of the vascular segments are separately identified in FIG. 5A. It is recognized that all or additional portions of the vasculature illustrated in FIG. 5A may be divided into corresponding segments. The user interface may utilize a mouse and cursor, keyboard, a microphone, a touch sensitive display, a trackball and the like. For example, when the cursor hovers over, or when a user clicks on a point within, the vascular district model 508, a segment boundary is designated to indicate the corresponding vascular segment 510-514. As one example, the segment boundary may represent a dashed line surrounding the boundary of the vascular segment. Additional or alternative segment boundary indicators may be utilized, such as changing coloring, changing shading, causing the vascular segment to enlarge (e.g., in a magnified form), causing the vascular segment to flash (e.g., bright and dark, between color and monotone, between solid and hollow, and the like).

Optionally, the IRIS system may provide suggested names for vascular segments. For example, the cursor may be held over a vascular segment. In response thereto, the IRIS system may provide one or more candidate vascular segment names. Additionally or alternatively, the IRIS system may provide one or more candidate names for a portion of the vascular network. Additionally or alternatively, the candidate names may be provided when other input components of the GUI designate a particular vascular segment. When a user selects a vascular segment, the name of the vascular segment is automatically populated within the segment label window 520.

A vascular segment 510-514 of interest may be designated in alternative manners. For example, the user may state the name of the vascular segment, utilize a keyboard to designate a vascular segment of interest. Additionally or alternatively, the PS worksheet 502 may be presented on a touch sensitive screen (e.g., on a tablet device, smart phone, touch sensitive computer monitor). The user may touch the vascular segment of interest with a finger or other indicator (pencil, light pen, etc.).

In the present example, the vascular segments 510-514 abut against one another in a continuous manner, without overlapping and without providing gaps there between. Optionally, the vascular segments 510-514 may overlap one another. As another example, vascular segments may be formed in successive overlapping manners, such that smaller vascular segments may afford identification of a smaller region, whereas larger vascular segments afford identification of larger regions.

Optionally, the IRIS system may allow manual adjustment of the size and/or shape of a vascular segment. For example, the user can modify an existing anatomical atlas and add new branches (including defining the length and thickness of the new branch). For example, once a user designates a particular vascular segment, the cursor may be utilized to click and drag a boundary of an individual vascular segment. For example, in the illustration of FIG. 5A, the user may desire to designate a portion of the vascular segment 510. To do so, the user would select the vascular segment 510. Next, the cursor could be used to select and grab the boundary of the vascular segment 510 (e.g., by holding down the right mouse button or left mouse button, selecting one or more keys on a keyboard, and the like). While holding the boundary of the vascular segment 510, the cursor may be moved to adjust the size of the vascular segment 510.

FIG. 5A illustrates one example of an anatomical atlas 506. However, it is recognized that the AA library includes multiple anatomical atlases associated with different vascular districts. Examples of alternative anatomical atlases 506 are illustrated in FIGS. 5B-5F, for the abdominal renal vascular district, foot vascular district, iliac femoral vascular district, thoracic vascular district and tibial peroneal vascular district.

As explained herein, the IRIS system enables the user to add additional or remove branches, nodes, vascular segments and other network components to/from the anatomical atlas.

In FIG. 5A, the PS worksheet 502 also includes a segment label window 520 that includes a list of the names of the segments 522 that are graphically illustrated in the graphical reporting area 504. The list of the names of the segments 522 may be collapsed or expanded based on a folder and subfolder organization. A vascular segment within the anatomical atlas 506 may be designated by selecting the corresponding segment 522 from the list in the segment label window 520.

The segment label window 520 also includes a local vascular district identifier 524 associated with the anatomical atlas 506. When a user desires to change the anatomical atlas 506 displayed, the user may do so by clicking on the local vascular district identifier 524. In response thereto, drop-down menu is presented of alternative local vascular districts. When an alternative local vascular district is selected, the graphical region 504 is updated with the new anatomical template.

Figure 5B:
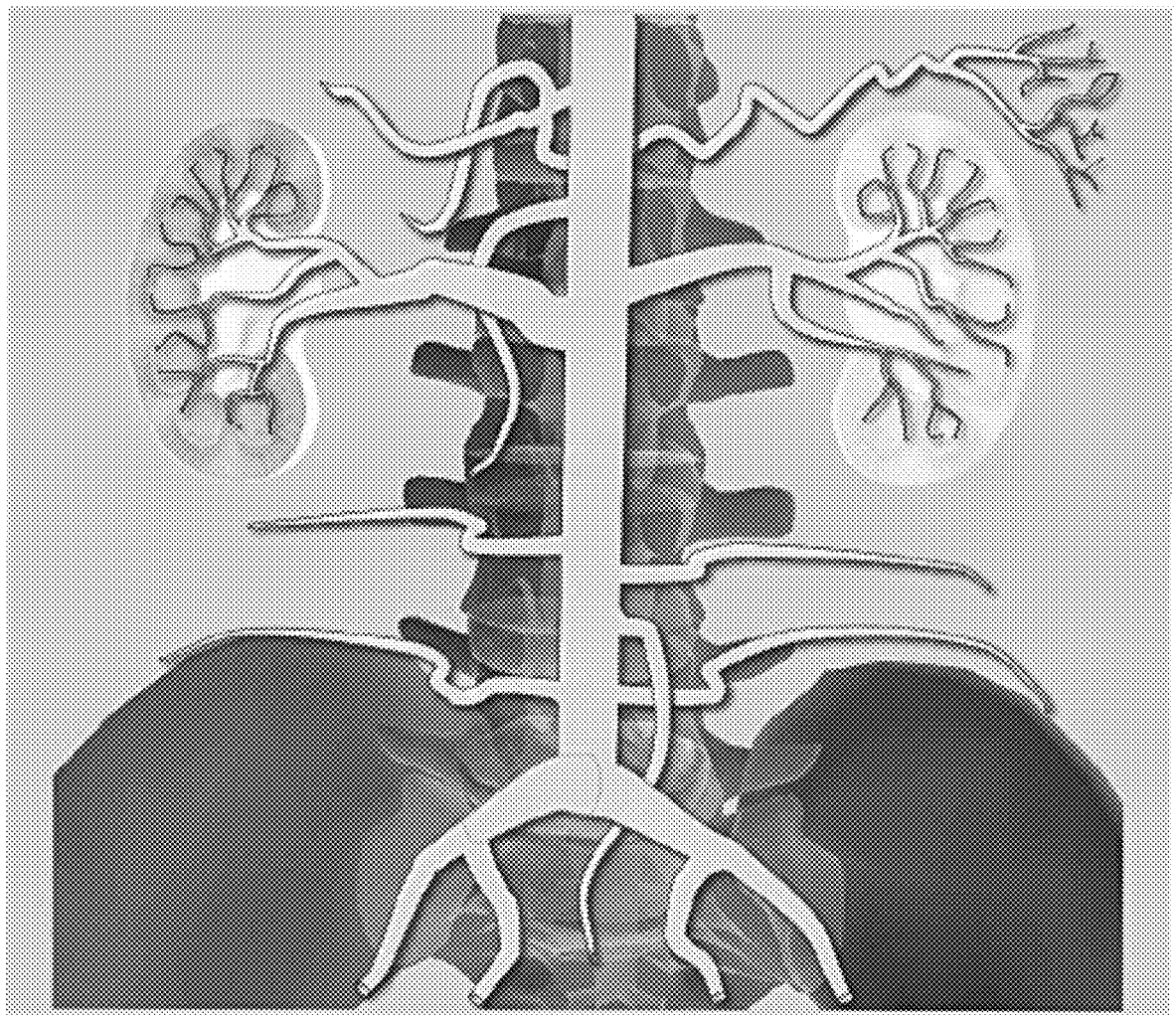
FIG. 5B illustrates an example of a procedure specific worksheet formed in accordance with an embodiment herein, with an anatomical atlas for the abdominal renal vascular district.

FIG. 5B illustrates an example of a procedure specific worksheet formed in accordance with an embodiment herein. In the example of FIG. 5B, an anatomical atlas is illustrated for the abdominal renal vascular district.

Figure 5C:
FIG. 5C illustrates an example of a procedure specific worksheet formed in accordance with an embodiment herein, with an anatomical atlas for a foot vascular district.

FIG. 5C illustrates an example of a procedure specific worksheet formed in accordance with an embodiment herein. In the example of FIG. 5C, an anatomical atlas is illustrated for a foot vascular district.

Figure 5D:
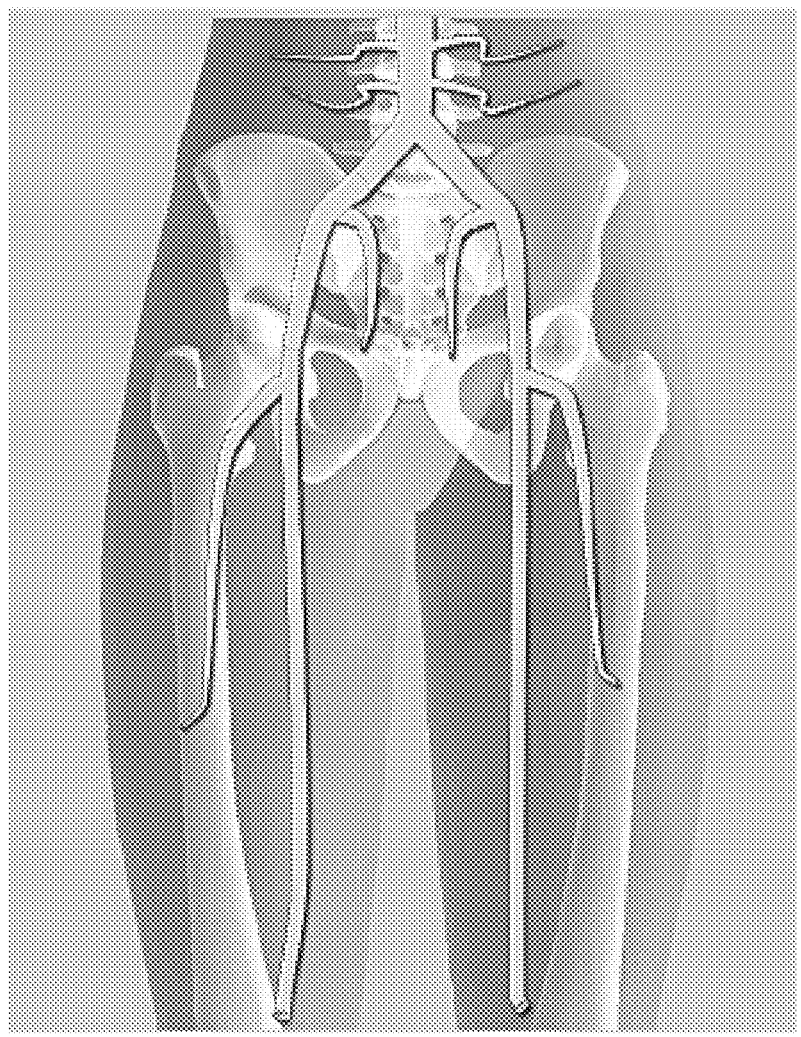
FIG. 5D illustrates an example of a procedure specific worksheet formed in accordance with an embodiment herein, with an anatomical atlas for the iliac femoral vascular district.

FIG. 5D illustrates an example of a procedure specific worksheet formed in accordance with an embodiment herein. In the example of FIG. 5D, an anatomical atlas is illustrated for the iliac femoral vascular district.

Figure 5E:
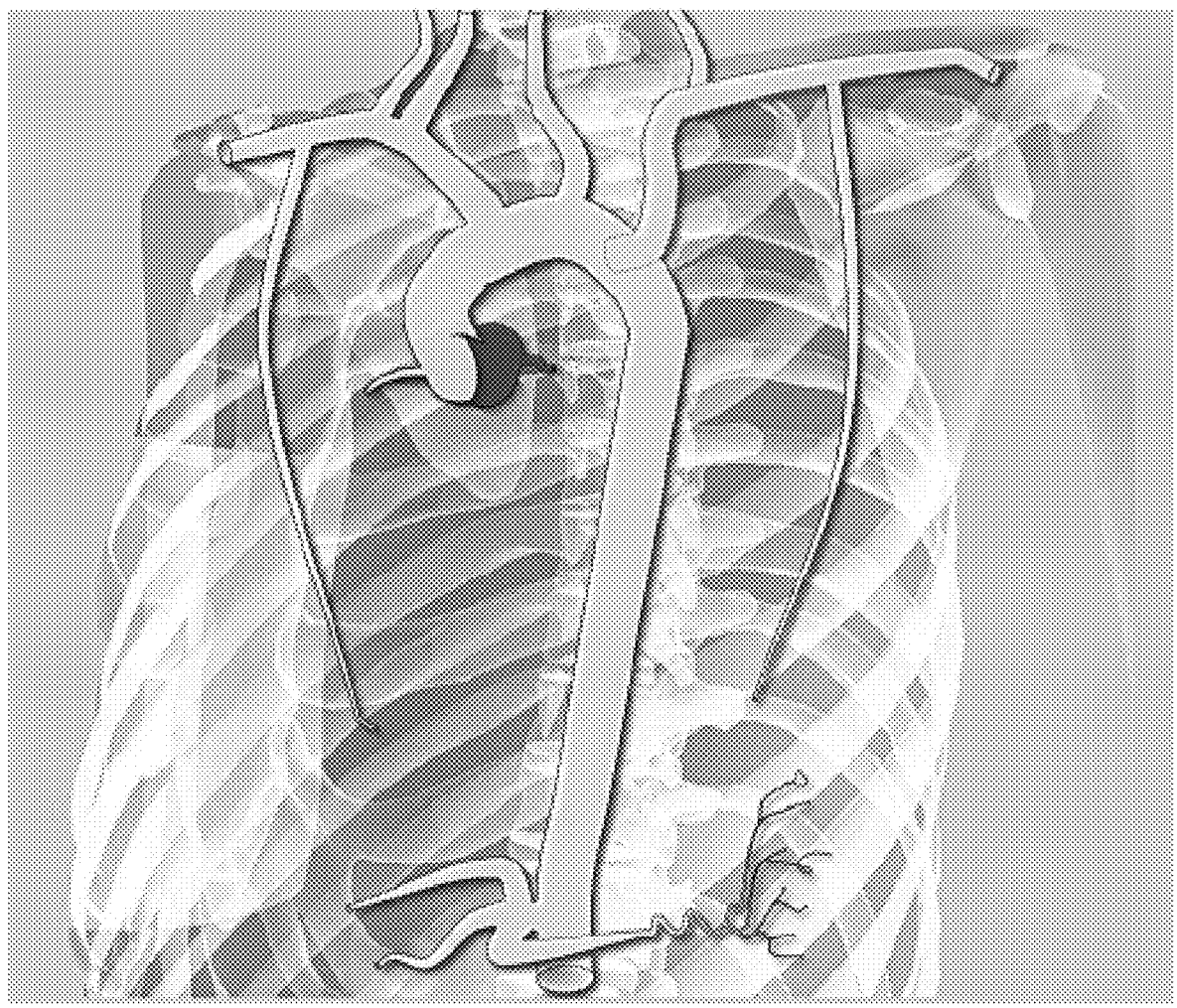
FIG. 5E illustrates an example of a procedure specific worksheet formed in accordance with an embodiment herein, with an anatomical atlas for the thoracic vascular district.

FIG. 5E illustrates an example of a procedure specific worksheet formed in accordance with an embodiment herein. In the example of FIG. 5E, an anatomical atlas is illustrated for the thoracic vascular district.

Figure 5F:
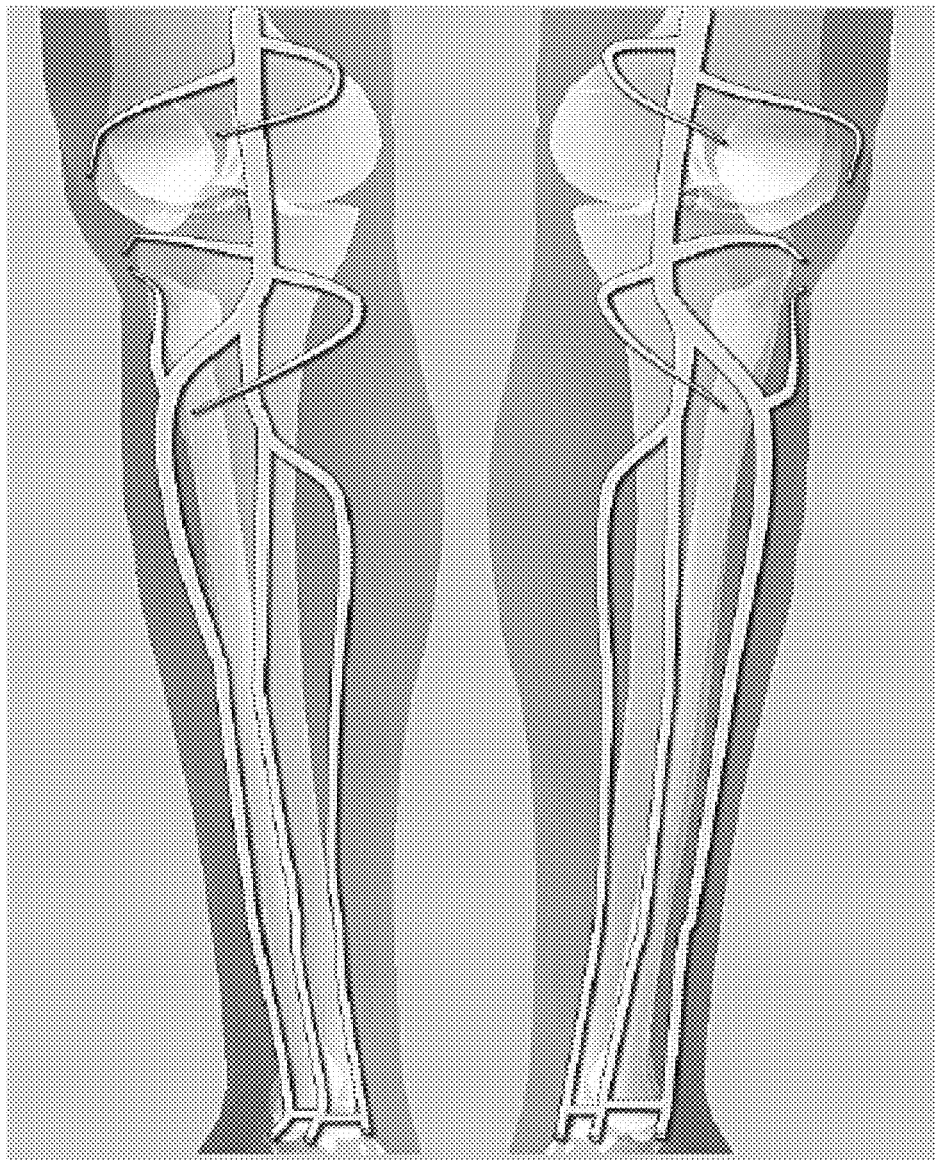
FIG. 5F illustrates an example of a procedure specific worksheet formed in accordance with an embodiment herein, with an anatomical atlas for the tibial peronial femoral vascular district.

FIG. 5F illustrates an example of a procedure specific worksheet formed in accordance with an embodiment herein. In the example of FIG. 5F, an anatomical atlas is illustrated for the tibial peronial femoral vascular district.

Figure 5G:
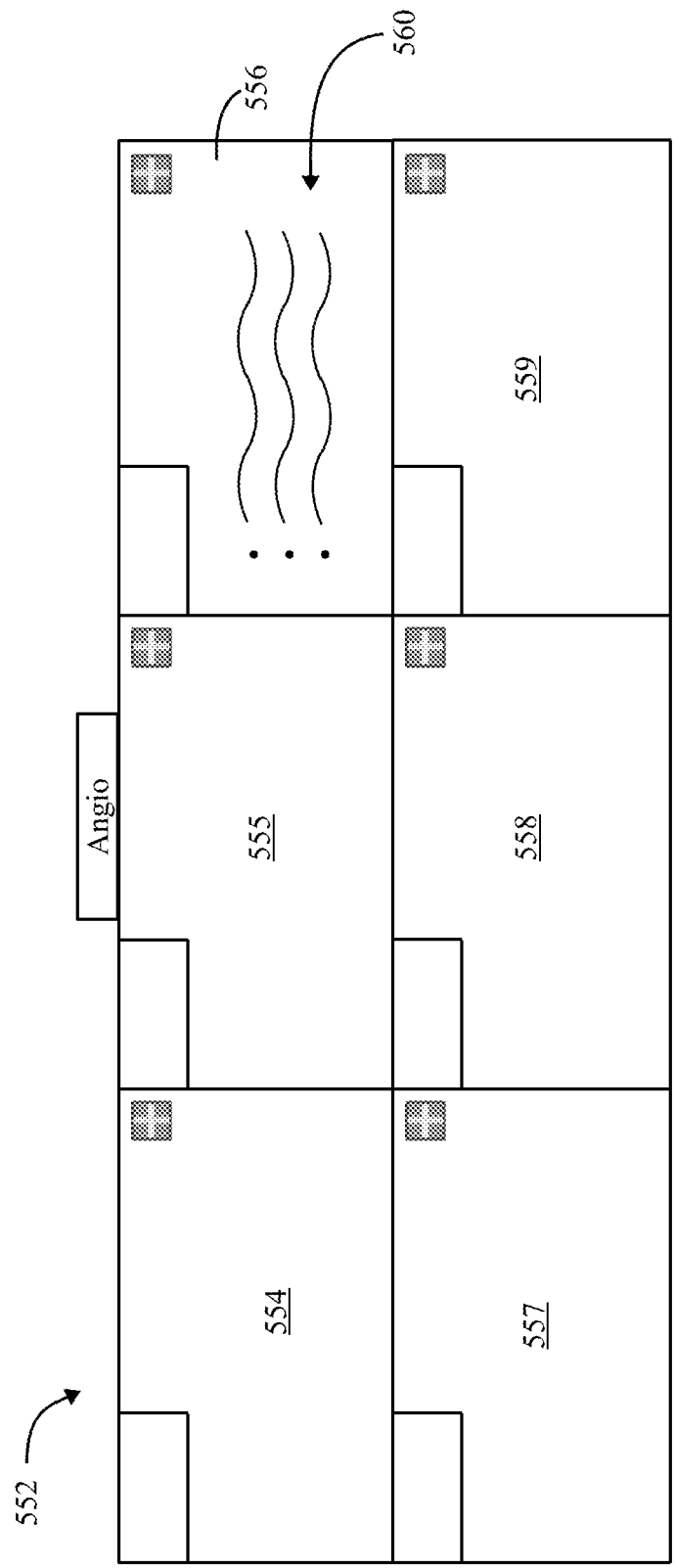
FIG. 5G illustrates an example of a text procedure specific (PS) worksheet within a final structured report formed in accordance with an embodiment herein.

FIG. 5G illustrates an example of a text procedure specific (PS) worksheet 552 within a final structured report 560 formed in accordance with an embodiment herein. The final structured report 560 is patient-procedure specific. The text based PS worksheet 552 includes one or more text reporting regions 554-559 that are uniquely associated with an anatomical atlas associated with a local vascular region in which the procedure or procedures have been or will be performed. Depending upon the procedure of interest, a corresponding one or more of the text reporting regions 554-559 contains a narrative description of the particular IR procedure of interest. The narrative description comprising a plurality of standardized statements. Examples of standardized statements include a standardized condition statement 561, a standardized medical device statement 563 and a standardized treatment statement 565.

Figure 5H:
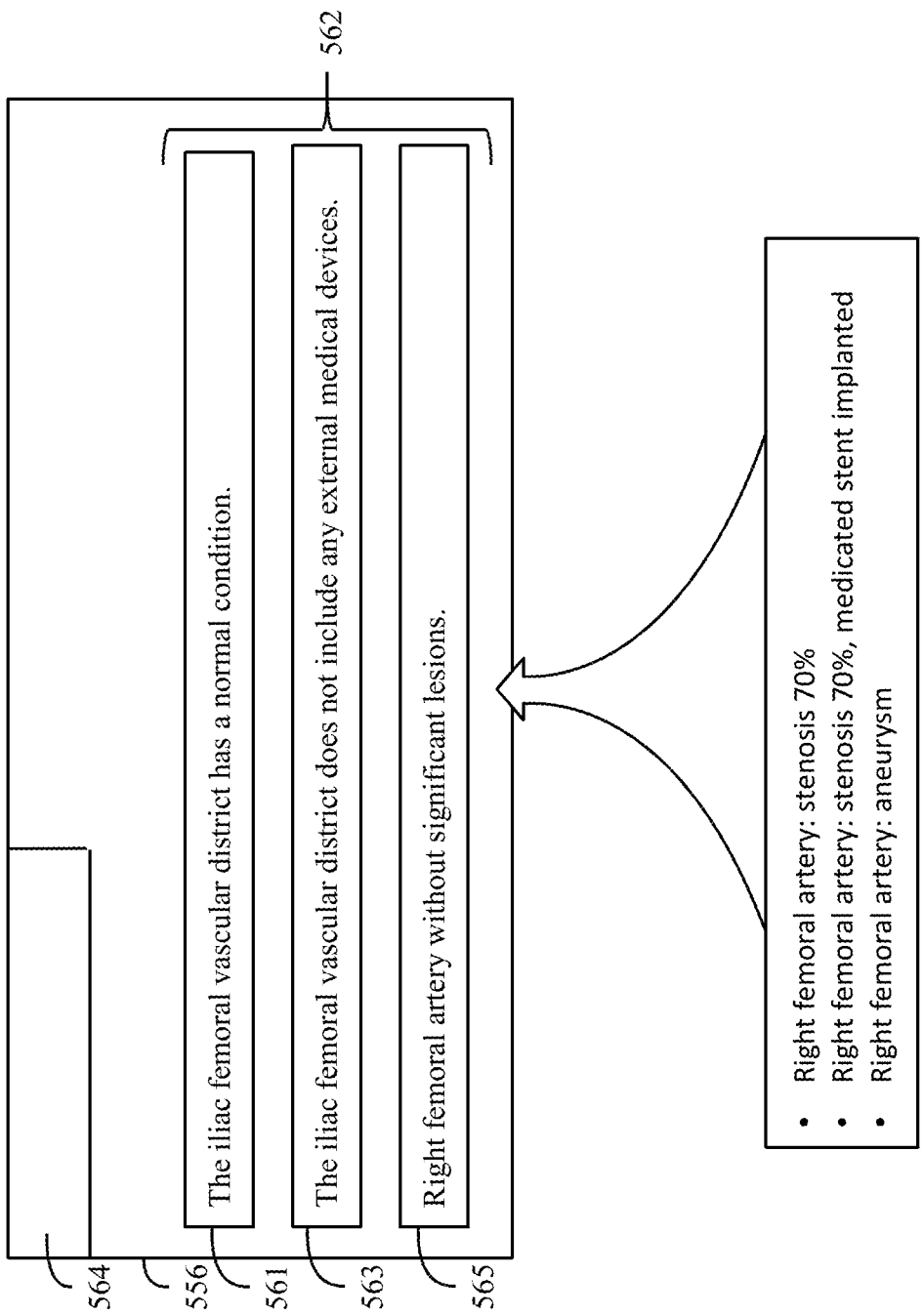
FIG. 5H illustrates a text reporting region in accordance with embodiments herein.

FIG. 5H illustrates a text reporting region 556 in more detail. The text reporting region 556 includes a district name section 564 designating a name of the vascular district, to which the text reporting region is associated. The text reporting region 556 also includes a set of text entry fields 562 that include standardized statements 561, 563, 565. The standardized statements 561, 563, 565 may be formatted as descriptive sentences or in other formats understandable to a physician. The standardized statements 561, 563, 565 are obtained from the anatomical atlas library 314, and represent information related to an interventional radiology procedure upon the vascular district of interest. The standardized statements 561 may describe a condition of the vascular segments within the vascular district of interest. The standardized statements 563 may also describe the existence or absence of medical devices and/or treatments (e.g., stents, ablation, etc.) within the vascular district. The standardized statements 565 may also describe base information about the corresponding procedure.

The standardized statements 561, 563, 565 are obtained from the anatomical atlas library 314 (FIG. 3). The AA library 314 retains various standardized statements associated with different local vascular districts. Optionally, more than one set of standardized statements may be provided for a single local vascular district based upon the type of procedure to be performed. By way of example only, an initial set of standardized statements 561, 563, 565 may include a statement that the vascular district of interest includes no abnormal conditions (e.g., aneurysms, no thrombosis and the like). The standardized statements 561, 563, 565 may also indicate that the vascular district includes no artificial medical devices (e.g., a stent) and has had no prior treatment applied thereto (e.g., an ablation). For example, FIG. 5H indicates the following base standardized statements: "The iliac femoral vascular district has a normal condition", "The iliac femoral vascular district does not include any external medical devices", and "The iliac femoral vascular district has not undergone any treatment".

Optionally, the standardized statements may include more than one statement concerning a district condition, more than one statement concerning the presence of external medical devices and more than one statement concerning past and present treatments applied to the district. Optionally, the standardized statements may concern subject matter other than conditions, medical devices and treatments. By way of example, the standardized statements may describe particular connections between different nodes, various branches and the like.

As explained herein, the IRIS system modifies one or more of the plurality of standardized statements based on the IR data collected through the data entry sheets. In addition, the IRIS system enables a physician to modify one or more anatomical atlas in the structured report. When an anatomical atlas is modified, the IRIS system modifies the corresponding standardized statement(s) 561, 563, 565 based on the modifications to the anatomical atlas.

By way of example, a modification to the standardized statement may indicate that a vascular district of interest includes an abnormal condition (e.g., an aneurysm). A modification to another standardized statement may indicate that an external medical device has been implanted (e.g., a stent). Another modification to the standardized statement may indicate that a treatment has been applied and ablation). The modifications to the standardized statements may include various levels of detailed description for the condition, medical device, treatment or otherwise. For example, the modification may identify the particular vascular segment, node, branch or other indicator of a particular location within a vascular district. The modification may also describe the condition, device, treatment or otherwise in great detail. For example, the modification may describe i) a degree of blockage, ii) a description of a thrombosis, iii) a description of the brand, type, size of a stent, iv) a description of a type, location and size of an ablation, or otherwise.

As explained above, each anatomical atlas 506 is divided into vascular segments, each of which is labelled. Optionally, a text reporting region associated with particular anatomical atlas may also have separate sets of standardized statements associated with vascular segments or other subsections of a vascular district.

The standardized statements may be automatically populated into a corresponding text reporting region of a worksheet within the structured report. Additionally or alternatively, the standardized statements may be presented as options in a pop-up menu, from which a user may select predefined statements to be added to a text reporting region of a worksheet within the structured report.

Figure 6:
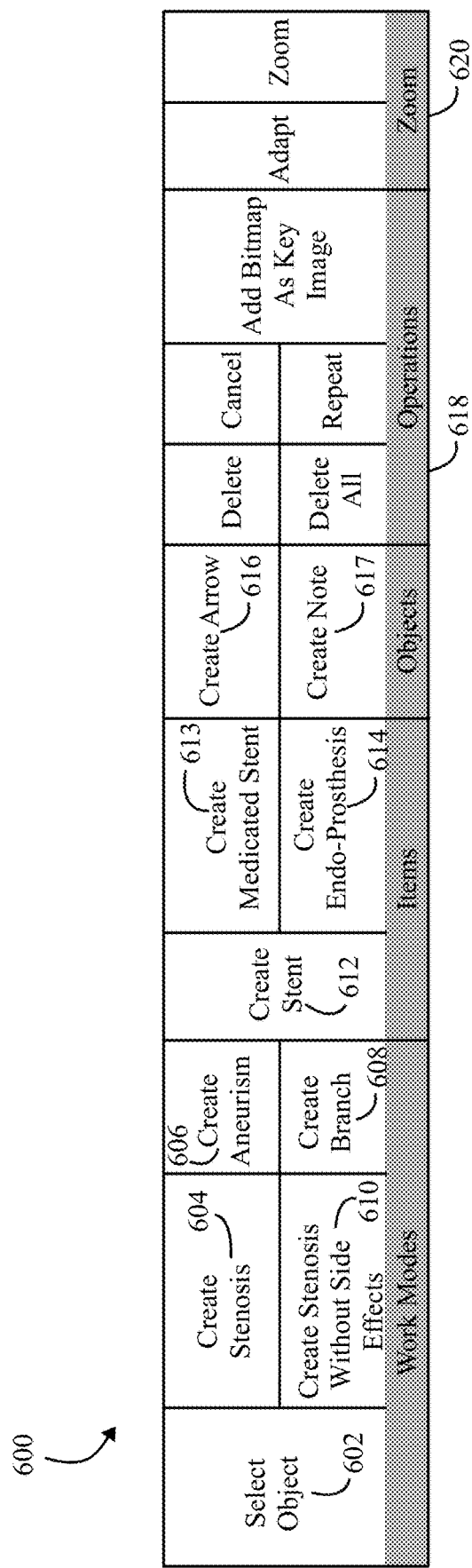
FIG. 6 illustrates an example of a toolbar that may be utilized in connection with editing the graphical reporting region of a procedure specific worksheet in accordance with embodiments herein.

FIG. 6 illustrates an example of a toolbar 600 that may be utilized in connection with editing the graphical reporting region 504 of a procedure specific worksheet 502 in accordance with embodiments herein. The toolbar 600 includes various icons to direct the IRIS system to perform associated functions. In the example of FIG. 6, a select segment icon 602 is utilized to select a portion of the vascular district model to be modified (e.g., a vascular segment).

A collection of work mode related icons is illustrated such as a create stenosis icon 604, create aneurysm icon 606, create branch icon 608 and a create stenosis without side effect icon 610. The icons 604-610 direct the IRIS system to perform corresponding functions, namely to create a stenosis, aneurysm or branch within the anatomical atlas 506. Additional or alternative work icons may be provided. Optionally, the operations for creating the stenosis, aneurysm, etc., may be initiated through other GUI components (e.g., a keyboard, spoken instructions, drop down menus, and the like).

When it is desirable to add a stenosis or aneurysm to a vascular segment, the vascular segment 510-514 is first selected. Next, the create stenosis or aneurysm icon 604, 606 is selected. In response thereto, a condition graphical indicator of the corresponding physiologic condition is superimposed upon the associated vascular segment. The condition graphical indicator may represent a model or template that graphically resembles a stenosis or aneurysm. The adjustment of the condition graphical indicators is discussed herein in more detail.

The toolbar 600 also includes icons associated with various items that may be added to the anatomical template. For example, device designator icons 612-614 correspond to a create stent operation, create medicated stent operation or create endo-prosthesis operation. When one of the device designator icon 612-614 is selected, the IRIS system overlays a device graphical indicator of the corresponding medical device onto the anatomical atlas within the currently selected vascular segment. The device graphical indicator may resemble a model or template of a stent or prosthesis or other medical device. The adjustment of the device graphical indicators is discussed herein in more detail.

The toolbar 600 includes additional icons associated with corresponding functions. For example, icons 616 and 617 enable arrows and nodes to be added to an anatomical atlas 506. The icons within an operations section 618 enable prior edits to be deleted, canceled repeated, etc. A zoom section 620 allows for adaptation operations and zoom operations. The toolbar 600 may include additional or alternative functionality.

Figure 7A:
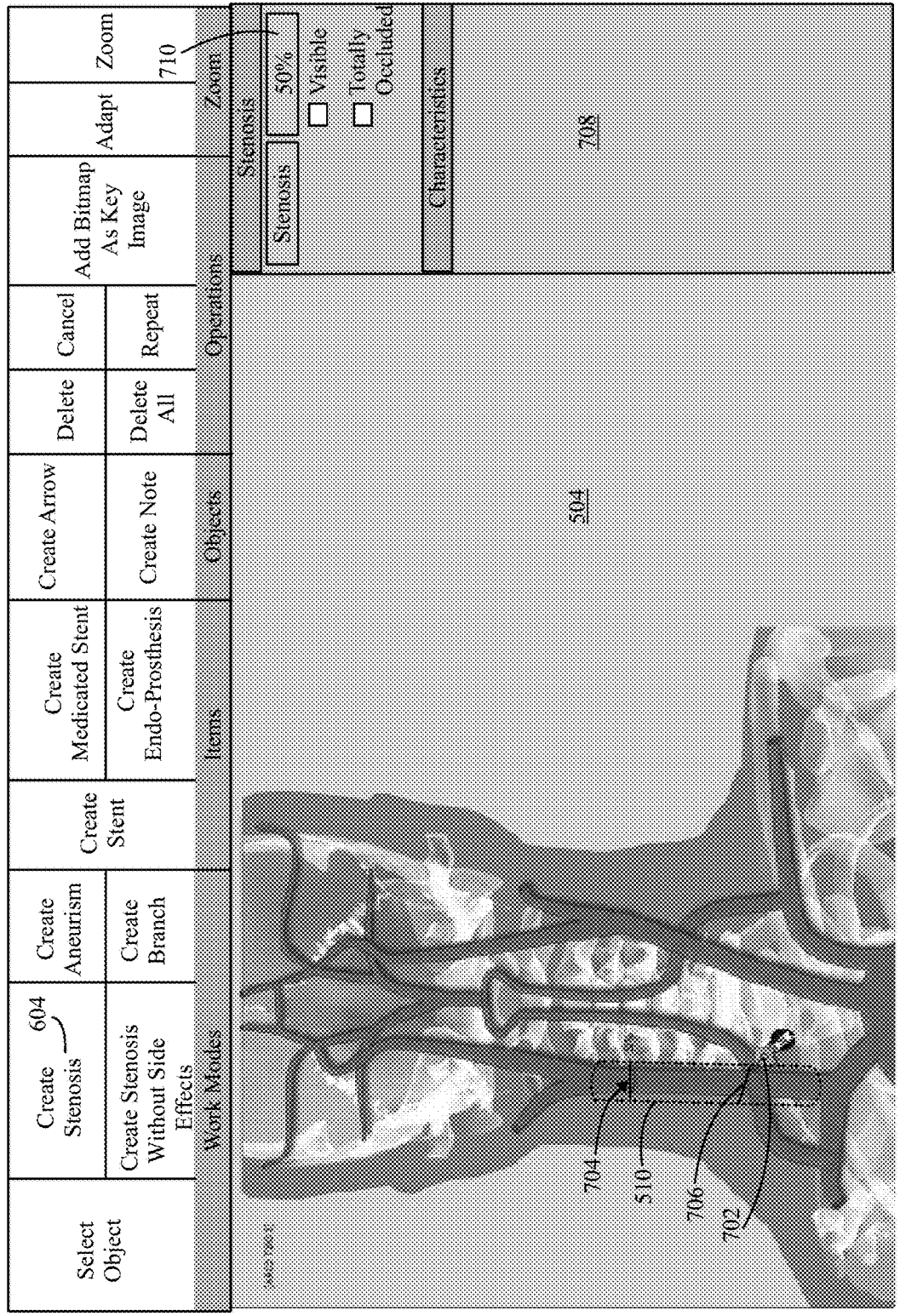
FIG. 7A illustrates an example of portions of the graphical reporting region that may be presented to the user while adding a physiologic condition to an anatomical atlas in accordance with an embodiment herein.
Figure 7B:
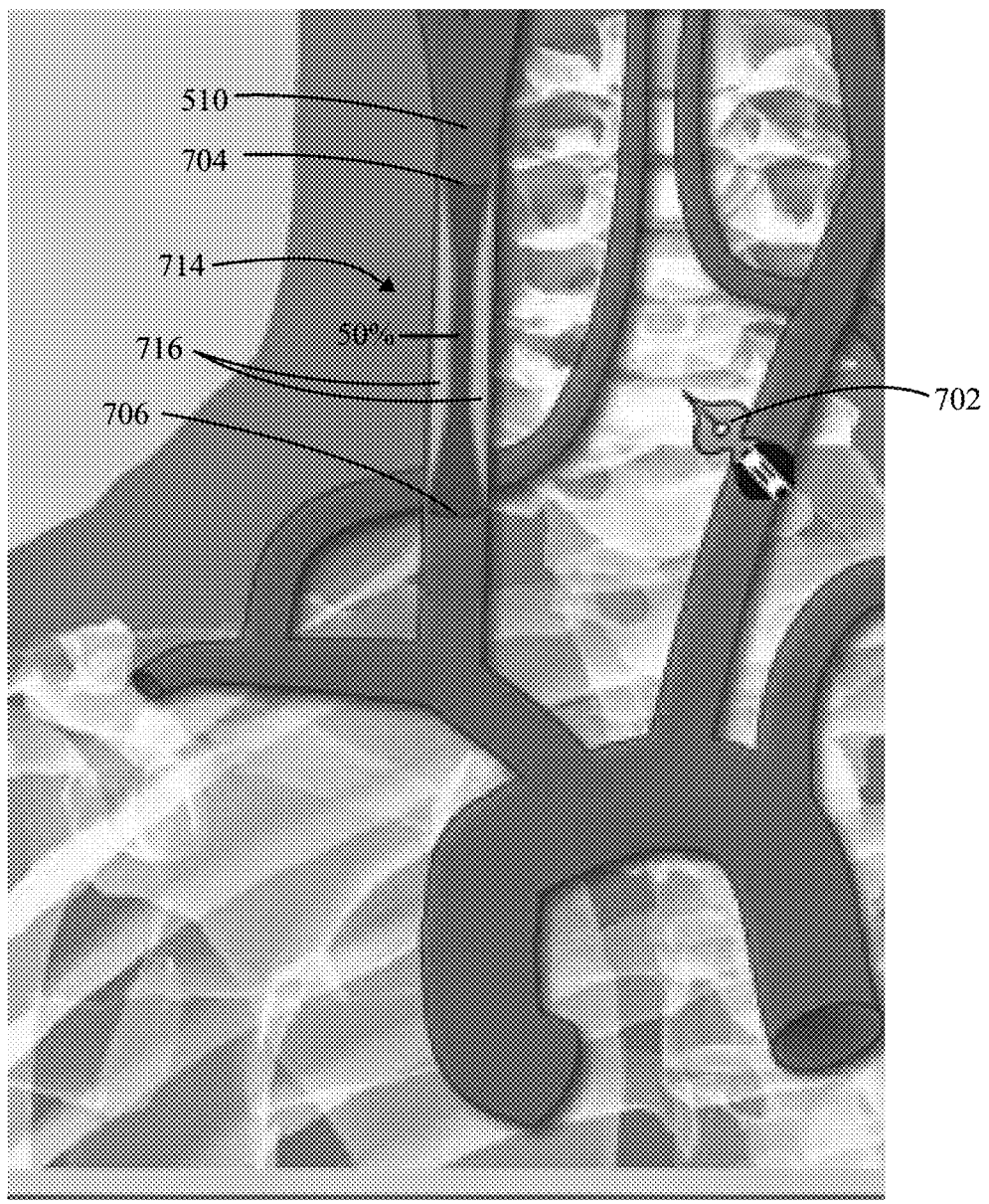
FIG. 7B illustrates a condition indicator corresponding to a graphical representation of a stenosis.
Figure 7C:
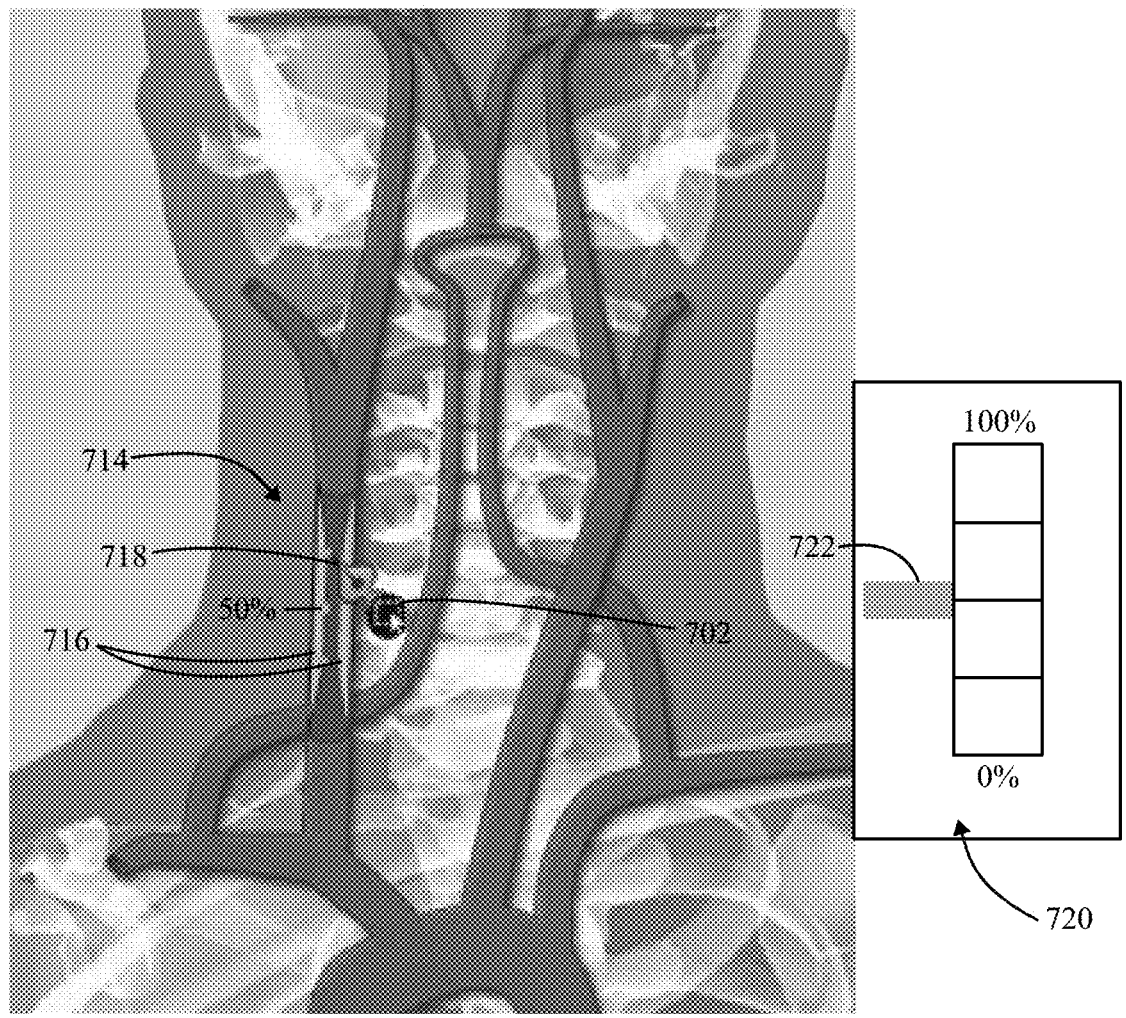
FIG. 7C illustrates a manner by which the amount of blockage in the condition indicator may be adjusted.

FIGS. 7A-7C illustrate examples of portions of the graphical reporting region 504 that may be presented to the user while adding a physiologic condition (e.g., aneurysm or stenosis) to an anatomical atlas. FIG. 7A illustrates a portion of the procedure specific worksheet 502 and the graphical region 504. The user selects the create stenosis tab 604 from the toolbar. Thereafter, a point within the vascular segment 510 is selected to designate a first end 704 for a stenosis (e.g. the cursor 702 may be moved to and clicked on the point). Next, a second end 706 of the stenosis is selected. For example, the cursor 702 is moved to, and clicked on a second point, within the vascular segment 510 to designate a second end 706 of the stenosis. Optionally, the stenosis may be drawn over a bifurcation or a trifurcation of a vessel. When at least the first end 704 is selected, a stenosis characterization region 708 is presented on the display to indicate one or more stenosis characteristics that are defined by stenosis characteristics fields 710. In the example of FIG. 7A, initial values for the stenosis characteristics fields 710 are populated, such as a 50% stenosis, having a percentage of visibility. Additional stenosis characteristics may be presented and/or alternative initial values defined. The user adjusts the percentage of the stenosis (e.g., blockage percentage) in various manners. For example, the percentage blockage may be adjusted by changing the numeric value in the stenosis characteristic fields 710. Additionally or alternatively, the user may adjust the percentage of the stenosis graphically by manipulating the cursor as illustrated hereafter in connection with FIGS. 7B and 7C.

FIG. 7B illustrates a condition indicator 714 corresponding to a graphical representation of a stenosis. The condition indicator 714 is overlaid upon the vascular segment 510 with the first and second ends 704 and 706 at the points designated (in connection with FIG. 7A). The condition indicator 714 is initially illustrated with the predetermined percentage of blockage 716 (e.g., 50%).

FIG. 7C illustrates a manner by which the amount of blockage in the condition indicator 714 may be adjusted. To graphically adjust the amount of stenosis, the user may click on (e.g., double-click on) the condition indicator 714. In response thereto, a scale 718 is presented on the condition indicator 714. The user may manipulate the cursor 702 to grab and adjust the scale 718 (e.g., upward or downward along a length of the condition indicator 714). As the cursor 702 drags the scale 718 along the condition indicator 714, the amount of blockage 716 is adjusted accordingly.

Optionally, additional or alternative graphics may be provided to enable adjustment of the percentage of blockage 716 through manipulation of the cursor and mouse. For example, a separate pop-up window may be presented with a scale. For example, a scale 720 may be provided in the graphical region 504 or elsewhere on the display. The scale 720 includes a level indicator 722 corresponding to a current percentage of blockage within the graphical stenosis 714. The cursor may be used to grab and drag the level indicator 722 along the scale 720 (between zero and 100% to adjust the amount of blockage). It is recognized that the scale 720 may be presented in alternative manners and may indicate the level of blockage in alternative manners in addition to or instead of a percentage measurement. The operations described in connection with FIGS. 7A-7C may be performed in order to characterize the condition of a vascular segment before a procedure, such as to indicate the location and amount of blockage before adding a stent or performing another procedure.

Figure 7D:
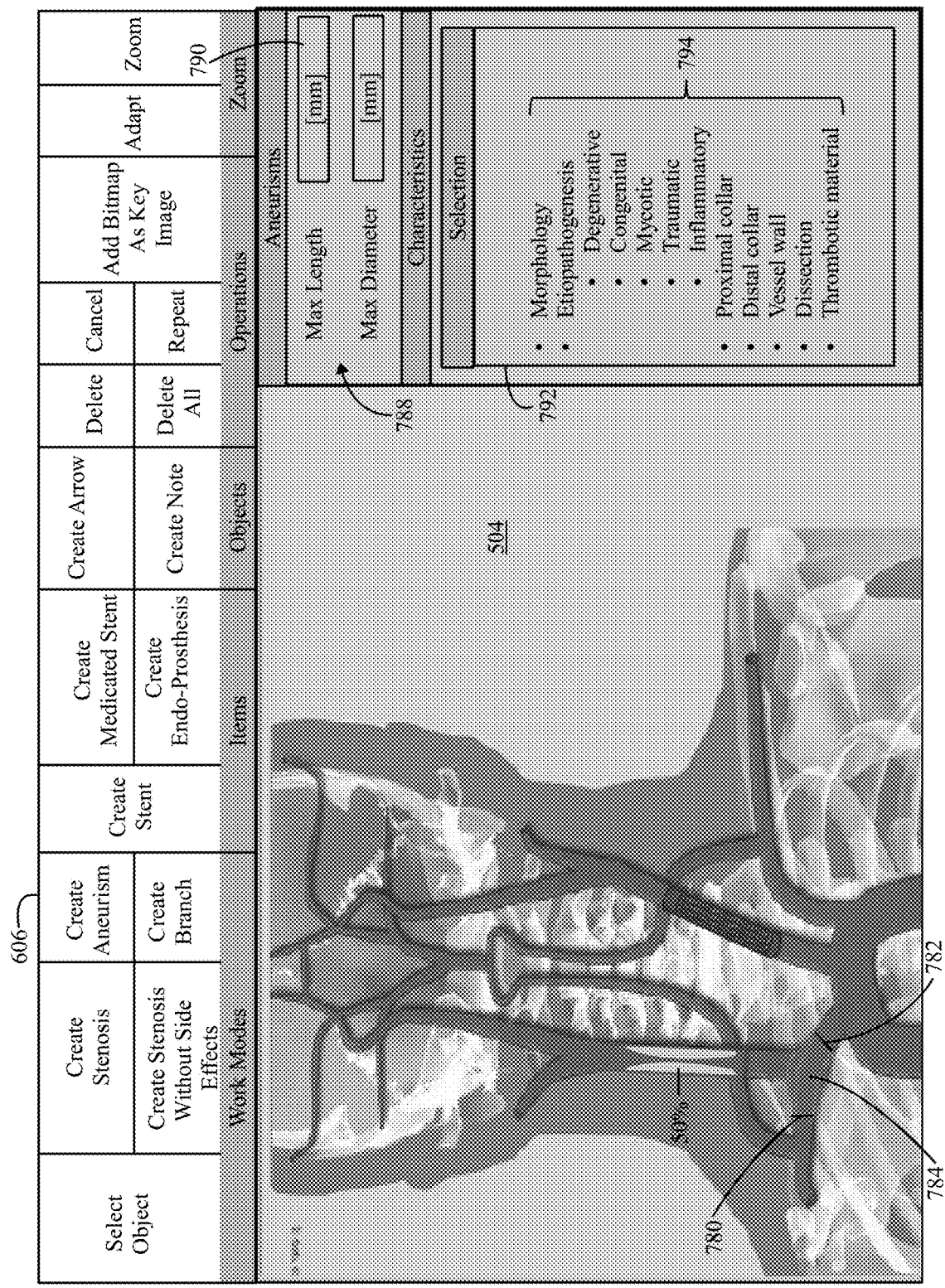
FIG. 7D illustrates an example of a portion of the anatomical atlas with a cauterized aneurysm superimposed thereon in accordance with embodiments herein.

FIG. 7D illustrates an example of a portion of the anatomical atlas 506 with a cauterized aneurysm superimposed thereon in accordance with embodiments herein. The operations described above in connection with FIGS. 7A-7C may be repeated in connection with designating an aneurysm location to be cauterized and inserting a cauterization aneurysm indicator at the corresponding location. To do so, the create aneurysm tab 606 is selected from the toolbar. Next, opposite ends 780 and 782 are designated. Once the ends 780 and 782 are designated, a condition indicator 784 is superimposed upon the corresponding portion of avascular segment. The condition indicator 784 may graphically resemble an aneurysm.

An aneurysm characterization region 788 is presented on the display to indicate one or more aneurysm characteristics that are defined by aneurysm characteristics fields 790. In the example of FIG. 7D, initial values for the aneurysm characteristics fields 790 are populated, such as a length in millimeters and a diameter in millimeters. Additional aneurysm characteristics may be presented and/or alternative initial values defined. The user adjusts the aneurysm characteristic fields in various manners. For example, the length and diameter of the aneurysm may be adjusted by changing the numeric value in the aneurysm characteristic fields 790. Additionally or alternatively, the user may adjust the length and/or diameter of the aneurysm graphically by manipulating the cursor (e.g., such as illustrated in connection with FIGS. 7B and 7C above).

Optionally, a cauterization indicator may be added as one type of therapeutic indicator such as when the aneurysm has previously been cauterized or the present procedure involves cauterizing the aneurysm. Various therapeutic indicators may be designated, such as from the toolbar or from a drop-down menu.

Optionally, a condition designation window 792 may be presented to allow the user to select predetermined descriptors for different types of conditions that are being added. For example, the windows 792 may be used to select a condition descriptor 794 such as to describe a particular type of aneurysm or other condition.

While not illustrated, it is understood that a similar process may be utilized to add other conditions to the vascular segments.

Figure 8:
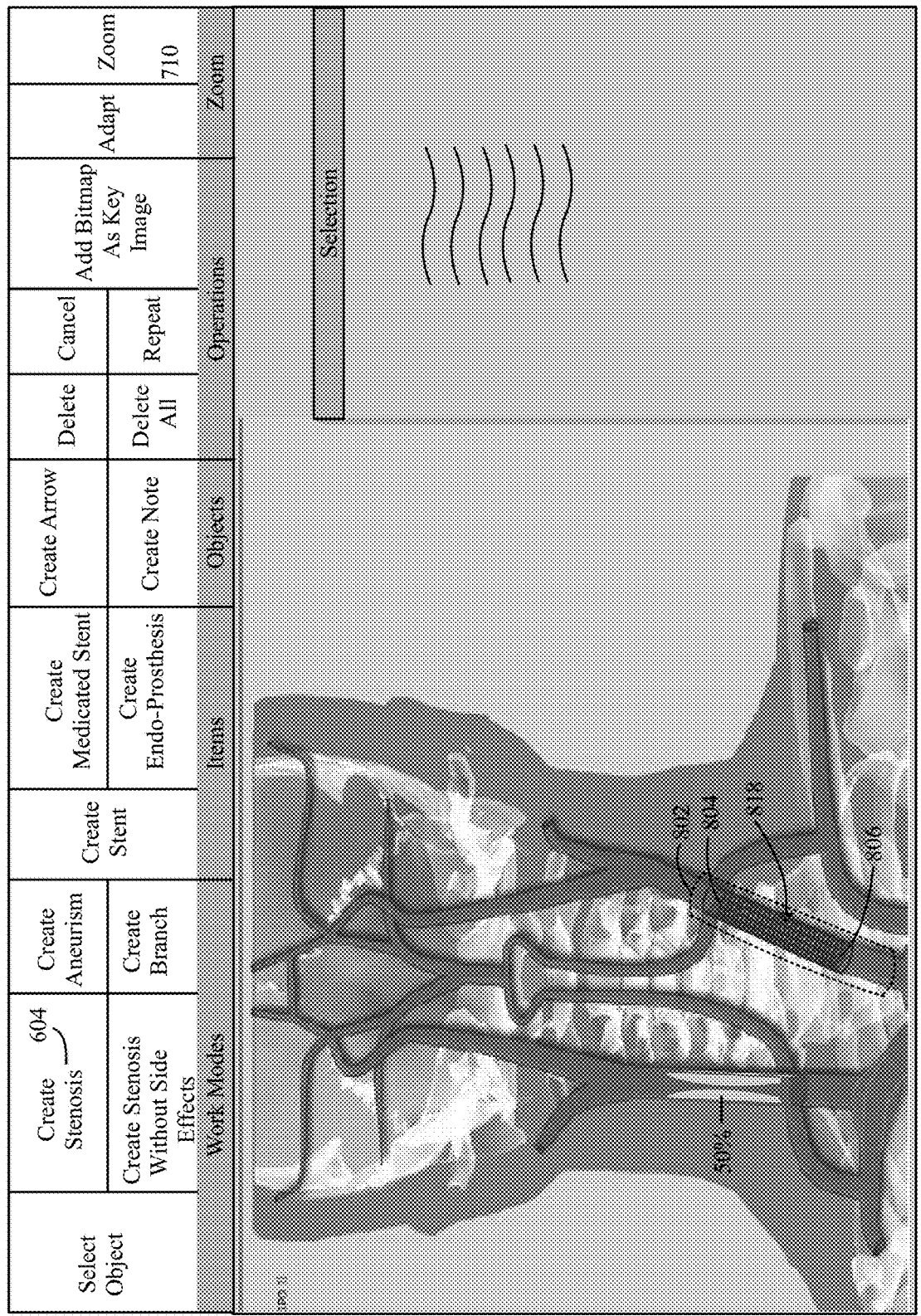
FIG. 8 illustrates an example of a portion of the graphical region that may be presented to the user while adding a device indicator to an anatomical atlas.

FIG. 8 illustrates an example of a portion of the graphical region that may be presented to the user while adding a device indicator to an anatomical atlas. The user begins by selecting the create object tab (e.g., device designator icons 612-614). Thereafter, a first end 804 for the object is designated. For example, the cursor 702 is moved to and clicked on a point within the vascular segment 802. Next, a second point is selected within the vascular segment 802 to designate a second end 806 of the object. For example, the cursor 702 is moved to, and clicked on a second point. The user then selects the type of object to be inserted such as by selecting the create stent tab 604 (or another create device tab) from the toolbar. In response thereto, a graphic device indicator 818 is presented corresponding to a graphical representation of a stent. The device indicator 818 is superimposed on the vascular segment 802 with the region between the first and second ends 804 and 806.

In the example of FIG. 8, initial values for the stent characteristics are utilized, such as a predetermined length, type, diameter, etc. The user may adjust the values for the stent characteristics by adjusting a numeric value in a stenosis characteristics fields (not shown). Additionally or alternatively, the user may adjust the stent characteristics graphically. Optionally, a scale (similar to the scale 720 in FIG. 7C) may be displayed that includes one or more level indicators corresponding values for characteristics of the device indicator 818. The cursor may be used to grab and drag the level indicators along the scale to adjust the levels. The operations described in connection with FIG. 8 may be performed before a procedure in order to characterize the condition of a vascular segment, such as to indicate the location and nature of a stent before adding the stent. Optionally, the operations of FIG. 8 may be performed after a stent has been added.

In accordance with embodiments herein, the IRIS system enables a user to create an anatomical atlas from "scratch". To do so, the user selects a create atlas tab. In response thereto, the IRIS system presents a blank anatomical atlas. The tool bar 600 is then used to create and position a network of vascular segments, branches and nodes of interest to form a user-modified anatomical atlas. Once the use-defined anatomical atlas is created, the user may name and save the user-modified anatomical atlas. The user-modified anatomical atlas may be saved in the AA library or elsewhere.

Figure 9A:
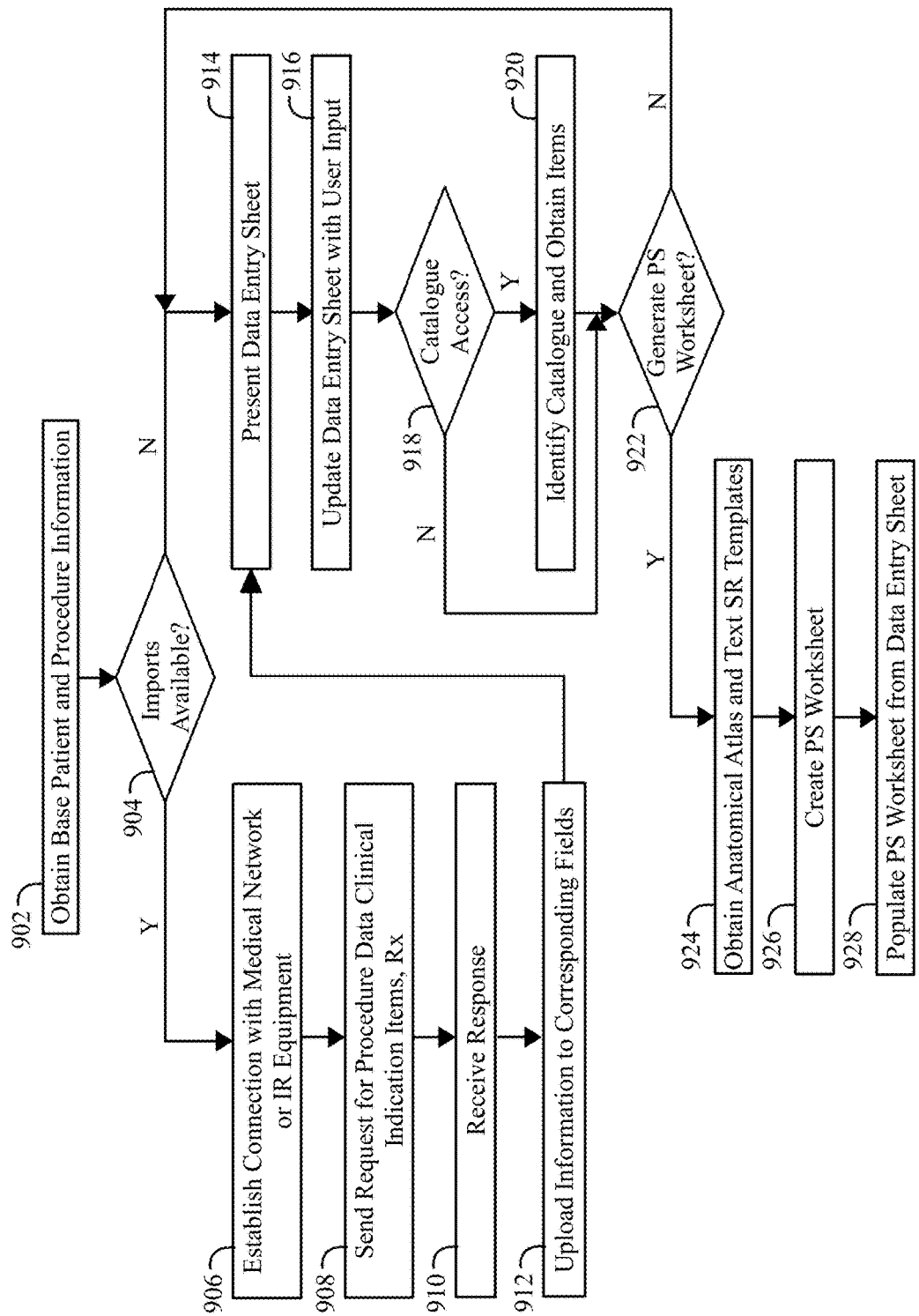
FIG. 9A illustrates a process carried out in accordance with embodiments for herein for generating structured reports.
Figure 9B:
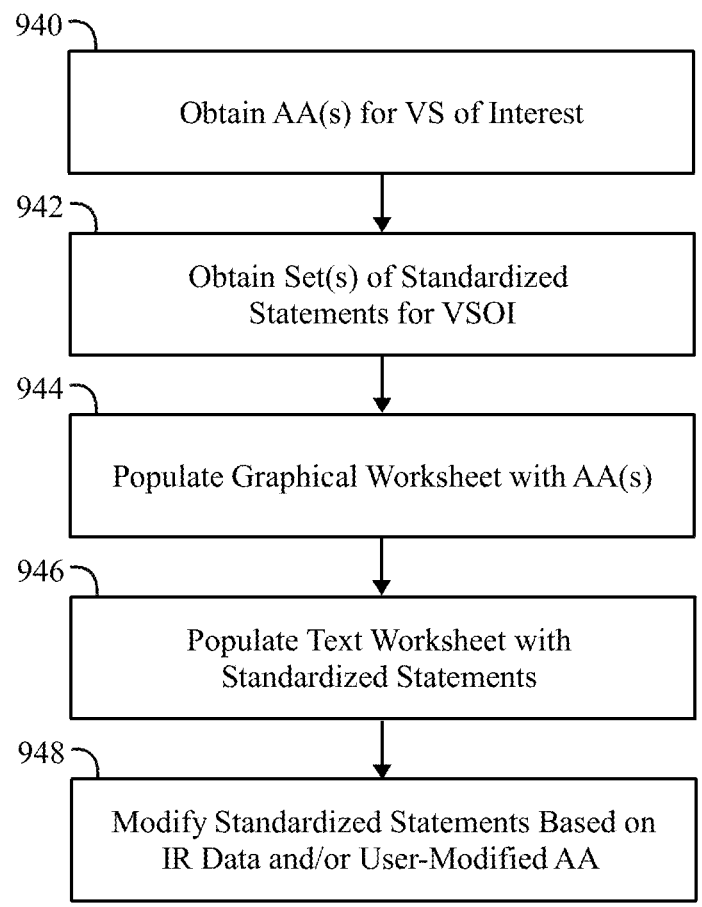
FIG. 9B illustrates a process carried out in accordance with embodiments for herein for generating structured reports.

FIGS. 9A and 9B illustrate a process carried out in accordance with embodiments for herein for generating structured reports. The operations of FIGS. 9A and 9B may be implemented by one or more processors such as the one or more processors within the IRIS system 122. All or a portion of the operations described in FIGS. 9A and 9B may be performed by the IRIS-PACS 120 (FIG. 1) and/or a workstation 125.

With reference to FIG. 9A, at 902, one or more processors of the IRIS system obtains base patient and procedural information. For example, the base information may represent the information entered on one or more of the data entry screens described in connection with FIGS. 4A-4E. At 904, the one or more processors of the IRIS system determine whether additional information is available at another storage location that may be imported into the structured report. For example, the IRIS system may be coupled to a medical network and/or IR equipment. At 904, when the IRIS system is coupled to another storage location, flow moves to 906. At 906, one or more processors of the IRIS system establish a connection with a medical network and/or interventional radiology equipment. At 908, the IRIS system sends a request to the medical network and/or IR equipment. The request includes identification information for the patient and/or the procedure for which the present structured report is being generated. For example, the request may include a unique patient identifier and/or a unique procedure identifier. The medical network and/or interventional radiology equipment accesses local records and determines whether information is available that matches the patient identifier and/or procedure identifier. If so, the information is returned to the IRIS system. Optionally, the request conveyed at 908 may include more than patient and/or procedure identifiers. For example, the request may include all or a portion of the base patient information and/or procedure information.

At 910, the IRIS system receives a response from the medical network and/or interventional radiology equipment. The response may indicate that no additional information is available. Optionally, the response may include additional procedure related information. As another option, the response may include additional clinical information. For example, as described herein in connection with at least one embodiment, and interventional radiology equipment may include fluoroscopy equipment, x-ray equipment, ultrasound equipment or another type of diagnostic equipment. The interventional radiology equipment may return operational information, such as start and stop times for when fluoroscopy equipment is utilized, position and orientation information for the fluoroscopy x-ray, ultrasound or other diagnostic equipment. For interventional radiology equipment that utilizes x-rays, the operational information may include the dose information. As another example, the interventional radiology equipment may include a contrast agent injection device. The contrast agent injection device may provide, as operational information, the times at which contrast agent was injected, the rate of injection, the nature of the injection (if known). Additionally or alternatively, the interventional radiology equipment may include PET or SPECT diagnostic equipment, that may return (as operational information) start and stop times for examinations, orientations of detectors, detector positions (relative to a reference point or coordinate system). In connection with utilizing PET or SPECT diagnostic equipment, the interventional radiology equipment may include injection equipment for injecting a radiopharmaceutical detected by the PET or SPECT diagnostic equipment. The PET or SPECT diagnostic equipment and/or the injection equipment may provide, as operational information, start and stop times for injections, injection dose, the type of radiopharmaceutical utilized and the like.

When information is received in the response at 910, at 912 the IRIS system uploads the relevant information to corresponding fields within the structured report. Various examples of fields are described herein in connection with FIGS. 4A-4G. The information received from the medical network and/or interventional radiology equipment may be directly loaded into the corresponding field within the various data entry sheets of the structured report.

Returning to 904, when the one or more processors of the IRIS system determine that data imports are not available, flow moves to 914. At 914, one or more data entry sheets are presented on a display. Examples of data entry sheets are described in connection with FIGS. 4A-4E. At 916, updates to the data entry sheets are received through the user interface. For example, the update may represent entering alphanumeric information through keyboard, graphical information or otherwise. The update at 916 may also represent attaching files to a data entry sheet, such as from a separate storage location.

At 918, the one or more processors of the IRIS system determine whether a catalog should be accessed to obtain information in connection with a present user input. For example, as discussed above, various types of catalogs are maintained in connection with different information utilized in interventional radiology procedures, such as a tool catalog 316, and procedure/action catalog 318, a clinical condition catalog 326 and a pharmaceutical catalog 330. The present examples are nonlimiting examples of the type of information that may be stored in catalogs. It is recognized that all or various portions of the foregoing information may be stored in various manners including in a common storage location, in a common catalog, in an alternative file structure and the like.

When one or more catalogs are available to be accessed at 918, flow moves to 920. Otherwise, the operation at 920 is skipped and flow advances to 922. At 920, the appropriate catalog or portion of the catalog is identified and the relevant items are obtained from the catalog. For example, as described in connection with FIG. 4A, when entering information regarding an access point, drop-down menus may be presented with options for the location of the access point, the manner of access, the type of the introducer, and a final condition. All or portions of the foregoing information may be stored in one or more catalogs, where the catalog entries are used to populate the corresponding drop-down menus. For example, a list of classes of IR procedure may be illustrated, from which the user may select a class designator. In response to receiving a class designator, the operations at 918 and 920 may be repeated to display a list of candidate IR procedures that correspond to the class of IR procedure designated by the class designator. When the user selects a candidate IR procedure, a corresponding procedure designator is recorded and used in connection with identifying a structured report template corresponding to a particular IR procedure (including generating a procedure specific worksheet).

As another example, as described in connection with FIG. 4D, a list of clinical conditions may be maintained to be presented in one or more drop-down menus when the user is filling out the clinical indication data entry sheet. At 920, the appropriate list of items is obtained from the corresponding catalog and presented to the user in a drop-down menu. Thereafter, the user selects one or more items from the drop-down menu to be added to the appropriate data entry sheet.

A procedure designator may be received at various points within the operations at 902-922, where the procedure designator designates an individual or particular IR procedure from a class of IR procedures. Additionally or alternatively, a class designator for a class of IR procedure may be received at 902, 910, 916 and 920. Examples of classes of IR procedures are described herein. For example, the procedure designator may be received at 902 when procedure information is obtained. Additionally or alternatively, a procedure designator may be received at 910 when a response to a request is received from a medical network and/or interventional radiology equipment. As a further option, the procedure designator may be received at 916 based on user inputs and/or 920 based on a selection from a catalog presented as a list in a pop-up menu or otherwise.

At 922, the one or more processors of the IRIS system determine whether to generate a procedure specific worksheet. The determination at 922 may be based on a user input. For example, a user may select a tab or icon indicating the desire to have a procedure specific worksheet generated. Additionally or alternatively, the determination at 922 may be made automatically based upon the amount of information that is already been provided on prior data entry sheets. For example, certain base information may be needed before a procedure specific worksheet can be generated. As an example, the base information may include identification of the patient, an identification of the local vascular district in which the IR procedure is to be performed, an identification of the nature of the IR procedure, the type of interventional radiology equipment utilized, additional or alternative information or a subset of the foregoing. Once a predetermined minimum amount of information is entered, the determination at 922 may be made to automatically generate a procedure specific worksheet. If so, flow moves to 924. If not, flow returns to 914 where the user is afforded the opportunity to enter additional information.

At 924, the one or more processors of the IRIS system obtains a structured report template. For example, the processors automatically identify a structured report template corresponding to the particular IR procedure based on at least one of the procedure designator or class designator. By way of example, a class designator may be used to identify an individual structured report template when the class designator corresponds to a single individual IR procedure, and/or all of the individual IR procedures within the class of IR procedure correspond to a common structured report template. The structured report template includes one or more graphics worksheet that includes a graphical region displaying an anatomical atlas for a non-coronary vascular district of interest that is designated by at least one of the particular IR procedure or the IR data. The structured report template also includes one or more text worksheet that includes one or more text report regions, each of which corresponds to a vascular district. The text report regions contain a narrative description of the particular IR procedure, the narrative description comprising a plurality of standardized statements, the method further comprising modifying one or more of the plurality of standardized statements based on the IR data collected through the data entry sheets.

The anatomical atlas is obtained from the anatomical atlas library 314 (FIG. 3). The anatomical atlas may be identified based upon various qualifications, such as an identification of the local vascular district in which the procedure is to be performed and/or the nature of the procedure. As another example, the anatomical atlas may be identified based on the location at which an angiogram is performed. As described above in connection with FIG. 4A, when entering procedural data on the data entry sheet 402, the user enters information in an angiogram region 412. The angiogram region 412 includes interventional radiology specific data entry fields for the angiogram location, the type of injection used with the angiogram, the quantity of contrast and the rate at which contrast is injected. At 924, the information within one or more of the data entry fields within the angiogram region 412 may be utilized to identify a particular anatomical template. As one example, the location may be designated as a cerebral angiography and/or the type of injection may be indicated as intra-arterial digital subtraction angiography. When a cerebral angiography is designated as the angiogram location, the corresponding anatomical atlas may correspond to the cerebral vascular system.

Optionally, at 924, more than one anatomical atlas may be identified. For example, when a procedure involves multiple vascular districts, at 924, the anatomical atlas for the corresponding multiple sectors will be obtained.

Optionally, additional or alternative information may be utilized as a basis to identify which anatomical atlas or templates are provided in the procedure specific worksheet.

At 926, the procedure specific worksheet is created. FIGS. 7A-7D illustrate an example of a procedure specific worksheet associated with a cerebral interventional radiology procedure. The cerebral IR procedure may involve diagnosis and treatment of various conditions within the cerebral vascular district.

With reference to FIGS. 7A-7B, an anatomical atlas is added to a graphical region within the procedure specific worksheet. At 928, the one or more processors of the IRIS system populates additional fields within the procedure specific worksheet from the data entry sheets. Thereafter, flow may branch in various directions. For example, a procedure specific worksheet may be presented on the display to the user. Additionally or alternatively, flow may return to 914 where the present data entry sheet is continued to be presented for the user to enter additional patient and procedure information. Optionally, at 928, flow may branch to 904 where it is again determined whether information is available to be imported into the procedure specific worksheet. For example, information may have been entered during the operations at 914 through 928 that may enable the IRIS system to identify a medical network (e.g., a radiology information system or a database stored on another system or server) and/or interventional radiology equipment that may contain patient or procedure information of interest. When the foregoing condition exists, the operations at 906-912 may be repeated.

It is recognized that the procedure will be scheduled utilizing an external information system. The external information system then transfers the procedure information to the IRIS system in the worklist page. Also, initial data (e.g., anagraphic patient data, scheduled procedure data, previous examinations) are obtained from a "historical" database stored on the IRIS system and/or from another database stored on a radiology information system. Also, it is recognized that the collection of procedural related data starts before the procedure begins and ends with the report writing after the procedure has ended.

FIG. 9B illustrates a more detailed illustration of the operations to generate the graphical and text worksheets within the structured report in accordance with an embodiment herein. The operations of FIG. 9B may be performed during the operations 924 and 926 of FIG. 9A.

At 940, the one or more processors obtain the anatomical atlas or atlases for a vascular district of interest from the AA library. As explained herein, the anatomical atlas is identified based on the particular IR procedure designated to be performed. When the particular IR procedure corresponds to an anatomical region that extends across more than one vascular district, multiple anatomical atlases are obtained.

At 942, the one or more processors obtain a set of standardized statements that correspond to the anatomical atlas identified at 940. When more than one anatomical atlases identified at 940, more than one set of standardized statements are obtained. The set or sets of standardized statements are presented within corresponding text reporting regions (e.g., 554-559 in FIG. 5G) on the text worksheet within the structured report.

At 944, the graphical worksheet is populated with one or more anatomical atlas, such as illustrated in FIG. 5A. The multiple anatomical atlases may be presented at separate tabs in the structured report, or alternatively presented on a common worksheet/window. For example, when a single procedure spans multiple vascular districts corresponding to all or a portion of the vascular districts illustrated in FIGS. 5B-5F, separate worksheets within the structured report may be formed for each vascular district with the corresponding anatomical atlas populated into the corresponding worksheet. The user may switch between the worksheets and anatomical atlases by selecting a corresponding tab on the page.

At 946, the text PS worksheet is generated and populated with one or more standardized statements. A set of standardized statements associated with a particular vascular district may be presented in one text reporting region, such as one of text reporting regions 556-559.

At 948, the one or more processors monitor the user interface of the IRIS system for inputs from the user. The input may correspond to a modification to the anatomical atlas and/or text reporting region. For example, the user may enter modifications to the standardized statements through the text reporting regions 556-559. Additionally or alternatively, the user may enter modifications to the anatomical atlas through the graphical region 504. The operations of FIGS. 9A and 9B are described below in more detail in connection with FIG. 10.

Figure 10:
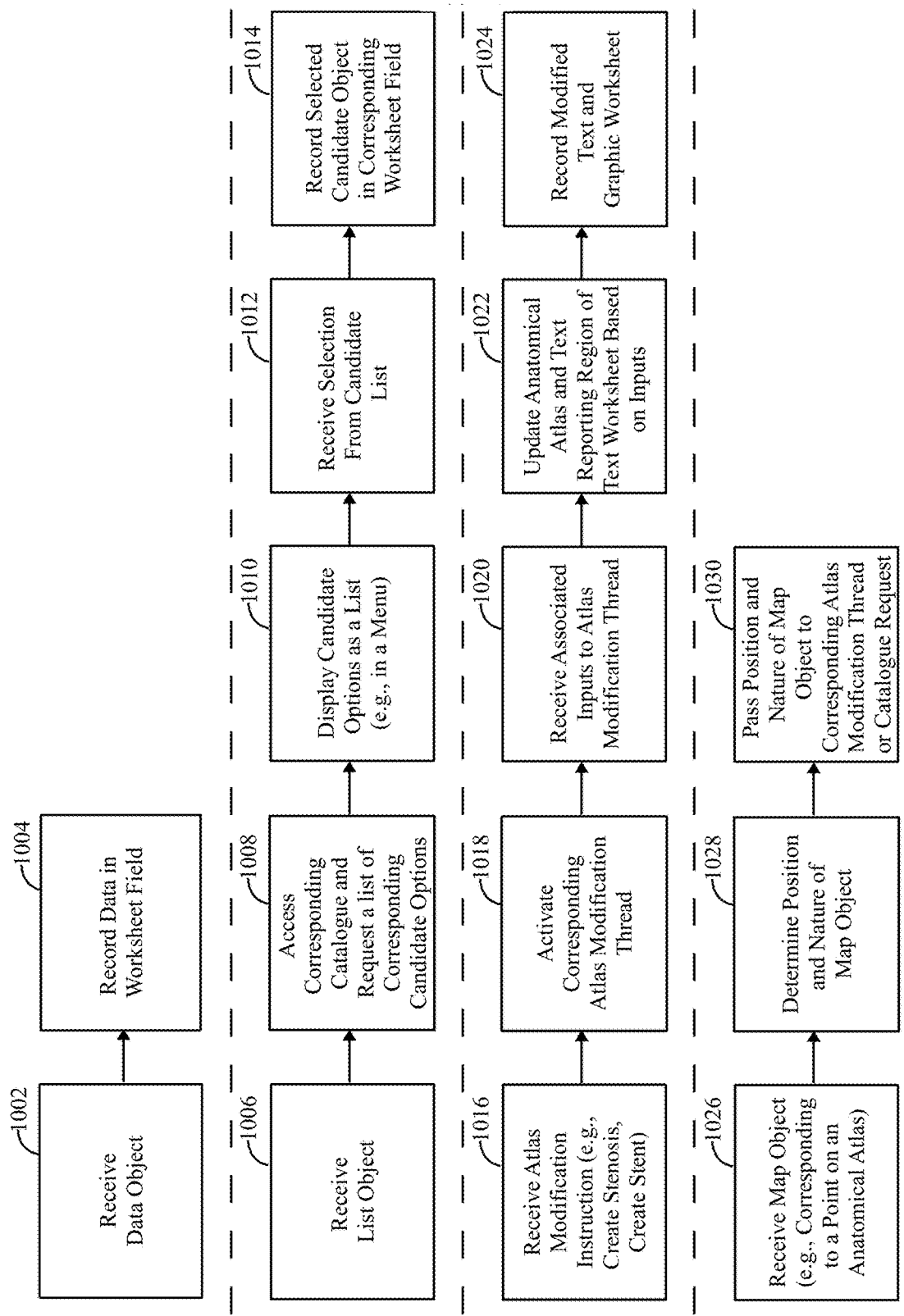
FIG. 10 illustrates a swim lane flow diagram of various processes that may be performed by the IRIS system in accordance with embodiments herein.

FIG. 10 illustrates a swim lane flow diagram of various processes that may be performed by the IRIS system in accordance with embodiments herein. The operations of FIG. 10 may be implemented by one or more processors such as the one or more processors within the IRIS system 122. All or a portion of the operations described in FIGS. 9A and 9B may be performed by the IRIS-PACS 120 (FIG. 1) and/or a workstation 125. The processes illustrated in FIG. 10 may be performed serially and/or in parallel while creating a structured report that includes a graphical worksheet and a text worksheet. FIG. 10 illustrates different processing sequences (moving from left to right across the figure) dependent upon an input received at the graphical user interface. The operations at 1002, 1006, 1016 and 1026 are initiated based upon different types of inputs received from the graphical user interface, namely data entry, a designation to display a list, a request to modify and atlas, a selection of a point on an atlas, respectively.

At 1002, the GUI is used by the user to enter data, referred to as a data object, when a user types, speaks or otherwise directly enters data. When a data object is received, the data is recorded into the corresponding data entry sheet and/or worksheet.

At 1006, the GUI is used by the user to select or otherwise indicate an item on the display that is linked or otherwise associated with a list of candidate options. For example, the user may select an icon or however the cursor over an active area that is linked to one or more catalogs. For example, in connection with FIG. 4D, an icon 449 may be selected when it is desired to add data to the clinical data region 448 as explained herein, when icon 449 is selected, a corresponding pop-up menu 451 is presented with a list of clinical conditions 453. At 1008, a corresponding catalog (e.g., clinical condition catalog 326 in FIG. 3) is accessed and a list of corresponding candidate options 328 are obtained. The list of corresponding candidate options is displayed in a menu (or other format) at 1010. For example, in FIG. 4D, the clinical conditions 453 are displayed in a pop-up menu 451. At 1012, the graphical user interface receives a selection from the candidate list. At 1014, the IRIS system records the selected candidate object (candidate clinical condition) in the corresponding field of the worksheet.

While the foregoing example is provided in connection with selecting a clinical condition, it is recognized that a similar process may be performed in connection with accessing any available catalog or library and selecting a corresponding candidate from an associated list of available options.

At 1016, the GUI is used by the user to enter an atlas modification request. By way of example, atlas modification request may be generated when the user selects a tab from the toolbar 600 (FIG. 6). As another example, atlas modification request may be created when a user performs predetermined operations upon the anatomical atlas within the graphical region of the worksheet. Additional or alternative operations may be utilized through the GUI to provide atlas modification request (e.g., through spoken commands, keyboard entries, trackball actions, mouse key selection sequences and the like).

At 1018, a corresponding atlas modification thread is activated. The activation of a thread is based upon the nature of the atlas modification request. For example, as described above, the toolbar 600 may afford the user various options, such as to create or modify conditions within vascular segments (e.g., create a stenosis or aneurysm). When the atlas modification request corresponds to creating a stenosis, aneurysm or other condition, a corresponding condition creation thread is initiated. The condition creation thread may include various inputs, such as a designation of the position for the condition, and one or more condition characteristics defining the nature of the condition (e.g., a percentage of blockage in a stenosis, a length of an aneurysm, and the like). At 1020, the atlas modification thread continues to operate while the user performs other operations, such as clicking on points within vascular segments within an anatomical atlas, typing parameter values for individual fields defining characteristics of a condition, device or otherwise. Once a sufficient number of inputs are received, at 1022, the atlas is updated by the atlas modification thread based on the inputs. By way of example, the modification may be to superimpose a graphical indicator of a condition on a vascular segment. Additionally or alternatively, the modification may be to draw a graphical indication of a vascular branch onto an anatomical atlas, remove a vascular branch or vascular segment from an anatomical atlas, change a path along which a vascular segment travels, and the like.

Additionally, at 1022, the text reporting region of the text based PS worksheet is updated based on the inputs. Continuing with the foregoing example, when the modification to the anatomical atlas is to draw a graphical indication of a vascular branch onto an anatomical atlas, the text reporting region is updated to describe the newly formed vascular branch. When the modification to the anatomical atlas is to remove a vascular branch or vascular segment from an anatomical atlas, the text reporting region is updated to remove a description of the branch or to indicated that the branch is closed or does not exist. When the modification to the anatomical atlas is to add a lesion, aneurysm or other condition, the text reporting region is updated to add a statement describing a location and nature of the lesion, aneurism or other condition (e.g., the branch or vascular segment). As the condition characteristics (e.g., size, shape, percentage blockage, opacity, etc.) are modified on the anatomical atlas, the text reporting region is updated to textually describe the modified lesion characteristics. When the modification to the anatomical atlas is to add a medical device, the text reporting region is updated to add a statement describing a location of the medical device (e.g., the corresponding branch or vascular segment). As the medical device characteristics (e.g., size, shape, etc.) are modified on the anatomical atlas, the text reporting region is updated to textually describe the modified device characteristics.

At 1024, the graphical PS worksheet and the text PS worksheet are saved as a modified anatomical atlas that includes user defined modifications (also referred to as a user-modified anatomical atlas.

Another example of an atlas modification instruction is the operations described above in connection with adjusting a percentage blockage within a stenosis through the use of a scale. The operations at 1016-1024 may be performed when a user opens and adjust a scale as in FIG. 7C.

At 1026, the GUI is used by the user to designate a map object. A map object represents a point or region on an anatomical atlas that is designated by a user, such as through operation of a keyboard, spoken commands, trackball, mouse and cursor and the like. For example, as discussed above, the user may designate one or more endpoints for a condition to be added to a vascular segment. The user may also designate one or more endpoints for a device (e.g., a stent) to be added to a vascular segment. When the user designates the endpoints, such designations represent map objects that are processed in accordance with the operations at 1026-1030.

At 1028, the IRIS system determines the position and nature of the map object. Examples of the position represent a discrete point, a region, a central point within a range, and the like. Examples of the nature of a map object represent designating a map points, orientations, links, regions and the like. For example, the map object may designate an orientation of a branch, designate a length of a stent, designate a region in which an aneurysm exists, and the like. It is recognized that an endpoint represents one example of a map object. Optionally, a map object may represent a vascular segment, branch, node or other region upon an anatomical atlas (or more generally within the graphical region displayed within a structured report).

At 1030, the position and nature information for the map object are processed accordingly. For example, when the map object is being entered in connection with an atlas modification thread, the position and nature of the map object are passed to the atlas modification thread. Additionally or alternatively, the position in nature of a map object may be processed in connection with a catalog request. For example, a map object may correspond to a cursor hovering over an icon or other active area associated with a list in one or more catalogs. When the IRIS system determines that the cursor is hovering over an active area or icon, the corresponding list of candidate options may be obtained and presented in a desired format. Additionally or alternatively, an icon or active area may be selected by positioning a cursor thereon and "clicking" on the icon/active area. In response thereto, the corresponding list of candidate options are obtained and presented in a desired format.

The operations illustrated in FIG. 10 are examples of one manner by which information may be obtained in connection with manipulating and anatomical atlas and entering data in connection with a structured report. It is understood that the functionality may be afforded in alternative manners.

The operations described above in connection with all of the FIGS. may be implemented by one or more processors such as the one or more processors within the IRIS system 122. All or a portion of the operations described herein may be performed by the IRIS-PACS 120 (FIG. 1) and/or a workstation 125.

Next, an example will be provided to illustrate one manner by which the standardized statements may be modified in the text workbook based on a user modified anatomical atlas. As changes are made to one or both of the text and graphical reporting regions, the corresponding changes are updated throughout the structured report. For example, when a change is made to an anatomical atlas, such as to add an aneurysm, thrombosis or other condition, the standardized statement describing the condition of the vascular district is similarly updated with the corresponding text reporting region on the text workbook within the structured report.

The text description of the modified vascular condition is obtained (at 948 in FIG. 9B from the anatomical atlas library), based on the selections by the user from the toolbar 600 (FIG. 6). For example, when a user selects the create aneurysm icon 606, the process determines that a modification is to be made to a vascular condition. As explained above, the user may use drop-down menus and/or the anatomical atlas to designate a vascular segment within a vascular district, in which the aneurysm is positioned. When a vascular segment is designated through the anatomical atlas, the process obtains the name of the vascular segment from the anatomical atlas library. Additionally or alternatively, the vascular segment name may be selected from a drop-down menu. As the graphical user interface is used to position an aneurysm on the anatomical atlas within a select vascular segment, the IRIS system tracks the vascular segment that has been updated. The text name of the corresponding vascular segment is added or modified within the condition statement within corresponding text reporting region.

The IRIS system also tracks the description of the change in condition. For example, when the user selected to create an aneurysm (from the toolbar), the IRIS system obtained a corresponding condition designator (also referred to as a candidate condition 328) from the clinical condition catalog 326. The condition designators include/represent a condition characteristic indicative of a nature of a condition of a vascular segment at a point of interest. Additionally or alternatively, a user may choose a clinical condition from a drop-down menu presented on the user interface. The options presented in the drop-down menu are obtained from the clinical condition catalog 326. When the user selects a corresponding condition from the drop-down menu, the IRIS system updates the condition statement 561 (with the name of the chosen clinical condition) within the text reporting region 556.

Additionally or alternatively, the IRIS system performs corresponding changes to the standardized device statement 563 based on user inputs to the anatomical atlas, from directly entering changes and/or selections from drop-down menus. For example, the user may choose from the toolbar to add a medical device to the anatomical atlas (e.g., create a stent created an endoprosthesis, etc.). Each device icon presented in the toolbar 600 is associated with a tool option within the tool catalog 316. When the user selects one of the device designator icons (e.g., the create stent icon 612, create medicated stent icon 613, create endo-prosthesis 614, etc.), the process obtains a corresponding text description of the device/tool 322 from the tool catalog 316. Once the user selects the device to be added, the user then selects the location at which to place the device. For example, the user may designate a vascular segment on the anatomical atlas. Additionally or alternatively, the user may select a location from a drop-down menu. When the location and device are selected, the process updates the standardized device statement 563 to form the modified device statement which describes the position and nature of the device (e.g., location, type, size of the stent).

Additionally or alternatively, the IRIS system performs corresponding changes to the standardized treatment statement 565 based on user inputs to the anatomical atlas, from directly entering changes and from selections in drop-down menus. For example, the user may choose from the toolbar to add a treatment indication to the anatomical atlas (e.g., record the location of an RF ablation). Each treatment icon presented in the toolbar 600 is associated with an action option within the procedure/action catalog 318. When the user selects a create ablation icon (not shown) or create stent icon, the process obtains a corresponding text description of the action 324 from the tool catalog 316. Once the user selects the treatment to be recorded, the user then selects the location at which the treatment took place. For example, the user may designate a vascular segment on the anatomical atlas. Additionally or alternatively, the user may select a treatment location from a drop-down menu. When the location and treatment are selected, the process updates the standardized device statement 565 to form the modified treatment statement which describes the position and nature of the treatment (e.g., location, type, size of the treatment).

The foregoing description concerns only a few examples of the types of conditions, devices and treatments that may be recorded in modified in connection with interventional radiology procedures. It is recognized that additional items may be recorded in connection with an interventional radiology procedure, in addition to or in place of recording modified conditions, devices and treatments.

In accordance with aspects described herein, a computer-implemented method is provided for managing an interventional radiology (IR), the method comprising:

receiving a procedure designator designating an individual or particular IR procedure from a class of IR procedures;
presenting one or more data entry sheets, the data entry sheets comprising IR data entry fields concerning IR procedural data and patient data, the data entry sheets formatted and defined to collect data related to IR
collecting IR data through the IR data entry fields associated with a patient and the particular IR procedure;
automatically identifying a structured report template corresponding to the particular IR procedure based on at least one of the procedure designator or class designator; and
automatically importing the IR data from the data entry sheets to corresponding fields in the structured report template to create a patient-procedure specific structured report.

In accordance with aspects described herein, the structured report template includes a graphical region displaying an anatomical atlas for a non-coronary vascular district of interest that is designated by at least one of the particular IR procedure or the IR data.

In accordance with aspects described herein, the method further comprising: receiving a class designator designating a class of IR procedure that includes one or more candidate IR procedures; and in response to the class designator, displaying a list of candidate IR procedures that correspond to the class of IR procedure designated by the class designator, the procedure designator being selected from the list of candidate IR procedures.

In accordance with aspects described herein, the method further comprising storing multiple anatomical atlases corresponding to procedures within the class of IR procedure, selecting an anatomical atlas from the multiple anatomical atlases, wherein the anatomical atlas selected corresponds to the particular IR procedure, and importing the anatomical atlas into the structured report template.

In accordance with aspects described herein, the procedure designators designate an angiogram as the particular IR procedure, and wherein at least one of the data entry sheets includes an angiogram region that is configured and formatted to receive information regarding angiograms.

In accordance with aspects described herein, the final structured report includes a text reporting region that contains a narrative description of the particular IR procedure, the narrative description comprising a plurality of standardized statements, the method further comprising modifying one or more of the plurality of standardized statements based on the IR data collected through the data entry sheets.

In accordance with aspects described herein, the final structured report includes an anatomical atlas corresponding to a non-coronary vascular district associated with the particular IR procedure, the method further comprising modifying the anatomical atlas.

In accordance with aspects described herein, the final structured report includes a text reporting region that contains a narrative description of the particular IR procedure, the narrative description comprising a plurality of standardized statements, the method comprising modifying one or more of the plurality of standardized statements based on the anatomical atlas.

In accordance with aspects described herein, the method further comprising displaying an option list that includes a list of at least one of interventional tools, interventional actions, vascular clinical conditions, or pharmaceutical agents available for use during the IR procedure, and entering user designation from the option list to the corresponding IR data entry field.

In accordance with aspects described herein, the method further comprising storing an interventional radiology structured workflow that includes multiple structured report templates associated with different IR procedures. In accordance with aspects described herein, wherein the interventional radiology structured workflow includes an anatomical atlas library having multiple anatomical atlases that correspond to separate and distinct vascular districts of interest, the anatomical atlases being non-patient specific. In accordance with aspects described herein, the interventional radiology structured workflow includes one or more catalogs containing option lists of at least one of interventional tools, interventional actions, vascular clinical conditions, or pharmaceutical agents available for use during the IR procedure.

In accordance with aspects described herein, a computer system is provided for managing an interventional radiology (IR), the computer system comprising:

memory to store program instructions and an interventional radiology structured (IRS) workflow including multiple structured reports, the structured reports associated with corresponding interventional procedures, the structured reports including sets of data entry sheets having a predetermined format and data entry fields uniquely associated with a corresponding aspect of an IR procedure;
a processor configured to execute the program instructions to:
receive a procedure designator designating an individual or particular IR procedure from a class of IR procedures;
collect IR data through the IR data entry fields associated with a patient and the particular IR procedure;
automatically identify a structured report template corresponding to the particular IR procedure based on at least one of the procedure designator or class designator; and
automatically import the IR data from the data entry sheets to corresponding fields in the structured report template to create a patient-procedure specific structured report.

In accordance with aspects described herein, the structured report template includes a graphical region displaying an anatomical atlas for a non-coronary vascular district of interest that is designated by at least one of the particular IR procedure or the IR data.

In accordance with aspects described herein, the processor receives a class designator designating a class of IR procedure that includes one or more candidate IR procedures; and in response to the class designator, displays a list of candidate IR procedures that correspond to the class of IR procedure designated by the class designator, the procedure designator being selected from the list of candidate IR procedures.

In accordance with aspects described herein, the memory further comprises multiple anatomical atlases corresponding to IR procedures within the class of IR procedure, the processor to select an anatomical atlas from the multiple anatomical atlases, wherein the anatomical atlas selected corresponds to the particular IR procedure, and import the anatomical atlas into the structured report template.

In accordance with aspects described herein, the final structured report includes a text reporting region that contains a narrative description of the particular IR procedure, the narrative description comprising a plurality of standardized statements, the processor further configured to modify one or more of the plurality of standardized statements based on the IR data collected through the data entry sheets.

In accordance with aspects described herein, the final structured report includes a text reporting region that contains a narrative description of the individual procedure, the narrative description comprising a plurality of standardized statements, the processor configured to modify one or more of the plurality of standardized statements based on the anatomical atlas.

In accordance with aspects described herein, the display is configured to display an option list that includes a list of at least one of interventional tools, interventional actions, vascular clinical conditions, or pharmaceutical agents available for use during the IR procedure, and the processor is configured to receive a user designation from the option list to the corresponding IR data entry field.

In accordance with aspects described herein, the interventional radiology structured workflow, stored in memory, includes one or more catalogs containing option lists of at least one of interventional tools, interventional actions, vascular clinical conditions, or pharmaceutical agents available for use during the IR procedure.

In accordance with aspects described herein, a computer system is provided for providing interventional radiology (IR), the computer system comprising:
  memory storing program instructions and an interventional radiology structured (IRS) workflow including multiple structured reports, the structured reports associated with corresponding interventional procedures, the structured reports including sets of data entry sheets, graphical worksheets and text reporting worksheets having a predetermined format and data entry fields uniquely associated with a corresponding aspect of an IR procedure;
  the memory further storing multiple anatomical atlases that correspond to separate vascular districts, the anatomical atlases including a vascular district model for vascular segments, branches and nodes within the corresponding vascular district; and
  a processor configured to execute the program instructions to:
    collect IR data through the data entry fields within one or more of the data entry sheets, the IR data corresponding to a select IR procedure and a vascular district of interest;
    obtain a candidate anatomical atlas from the multiple anatomical atlases based on the IR data, the candidate anatomical atlas illustrating the vascular district model associated with the select IR procedure; and
    create a structured report based on the IR data collected, the structured report including the candidate anatomical atlas illustrating the vascular district model associated with the select IR procedure.

In accordance with aspects described herein, the memory stores the anatomical atlases in a library with the anatomical atlases corresponding to separate and distinct vascular districts of interest.

In accordance with aspects described herein, at least a first anatomical atlas includes a vascular district model of vascular segments, branches the first anatomical atlas further includes a structural model of a portion of a human structural anatomy surrounding the vascular segments.

In accordance with aspects described herein, the processor: receives a condition designator indicating a point of interest in a vascular segment of the anatomical atlas, the condition designator indicative of a nature of a condition of the vascular segment; and superimposes a condition indicator on the vascular segment proximate to the point of interest, the condition indicator being indicative of the condition.

In accordance with aspects described herein, the condition designator corresponds to at least one of a stenosis or aneurysm. In accordance with aspects described herein, the processor: receives a device designator indicating a point of interest in a vascular segment of the anatomical atlas, the device designator including a characteristic indicative of a device applied to the vascular segment at the point of interest; and superimposes a device indicator on the vascular segment at the point of interest, the device indicator being indicative of the device applied to the vascular segment.

In accordance with aspects described herein, the processor: generates a text based procedure specific (PS) worksheet that includes one or more text reporting regions that are uniquely associated with a corresponding anatomical atlas associated with the local vascular region, the text reporting region containing a narrative description of the individual procedure of interest, the narrative description comprising a plurality of standardized statements.

In accordance with aspects described herein, the processor: generates a text based procedure specific (PS) worksheet that includes a standardized statement for at least one of a condition, medical device or treatment; and modifies the standardized statement based on a user modification to the anatomical atlas. In accordance with aspects described herein, the processor: generates a procedure specific worksheet that includes text reporting region; populates the text reporting region with a standardized statement for at least one of a condition, medical device or treatment; receives an input corresponding to a modification to at least one of the anatomical atlas and the text reporting region; and updates the standardized statement based on the input.

In accordance with aspects described herein, a computer implemented method is provided for providing interventional radiology (IR) structured report workflow management, the method comprising:
  storing, in memory, program instructions and an interventional radiology structured (IRS) workflow including multiple structured reports, the structured reports associated with corresponding interventional procedures, the structured reports including sets of data entry sheets, graphical worksheets and text reporting worksheets having a predetermined format and data entry fields uniquely associated with a corresponding aspect of an IR procedure;
  storing, in memory, multiple anatomical atlases that correspond to separate vascular districts, the anatomical atlases including a vascular district model for vascular segments, branches and nodes within the corresponding vascular district; and presenting, on a graphical user interface (GUI), data entry sheets that include data entry fields;

collecting IR data, utilizing the GUI, through the data entry fields within one or more of the data entry sheets, the IR data corresponding to a select IR procedure and a vascular district of interest;

obtaining a candidate anatomical atlas from the multiple anatomical atlases based on the IR data, the candidate anatomical atlas illustrating the vascular district model associated with the select IR procedure; and creating a structured report based on the IR data collected, the structured report including the candidate anatomical atlas illustrating the vascular district model associated with the select IR procedure.

In accordance with aspects described herein, the method further comprising storing the anatomical atlases in a library with the anatomical atlases corresponding to separate and distinct vascular districts of interest.

In accordance with aspects described herein, at least a first anatomical atlas includes a vascular district model of vascular segments, branches, the first anatomical atlas further includes a structural model of a portion of a human structural anatomy surrounding the vascular segments.

In accordance with aspects described herein, the method further comprising: receiving a condition designator indicating a point of interest in a vascular segment of the anatomical atlas, the condition designator indicative of a nature of a condition of the vascular segment; and superimposing a condition indicator on the vascular segment proximate to the point of interest, the condition indicator being indicative of the condition.

In accordance with aspects described herein, the condition designator corresponds to at least one of a stenosis or aneurysm.

In accordance with aspects described herein, the method further comprising: receiving a device designator indicating a point of interest in a vascular segment of the anatomical atlas, the device designator including a characteristic indicative of a device applied to the vascular segment at the point of interest; and superimposing a device indicator on the vascular segment at the point of interest, the device indicator being indicative of the device applied to the vascular segment.

In accordance with aspects described herein, the method further comprising generating a text based procedure specific (PS) worksheet that includes one or more text reporting regions that are uniquely associated with a corresponding anatomical atlas associated with the local vascular region, the text reporting region containing a narrative description of the individual procedure of interest, the narrative description comprising a plurality of standardized statements.

In accordance with aspects described herein, the method further comprising: generating a text based procedure specific (PS) worksheet that includes a standardized statement for at least one of a condition, medical device or treatment; and modifying the standardized statement based on a user modification to the anatomical atlas.

In accordance with aspects described herein, the method further comprising: generating a procedure specific worksheet that includes text reporting region; populating the text reporting region with a standardized statement for at least one of a condition, medical device or treatment; receiving an input corresponding to a modification to at least one of the anatomical atlas and the text reporting region; and updating the standardized statement based on the input.

It should be clearly understood that the various arrangements and processes broadly described and illustrated with respect to the FIGS., and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the FIGS., which illustrate example methods, devices and program products according to various example embodiments. These program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random-access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A computer system for providing interventional radiology (IR), the computer system comprising:

memory storing program instructions and sets of data entry sheets having a predetermined format and data entry fields uniquely associated with a corresponding aspect of an IR procedure, and the memory further storing multiple anatomical atlases that correspond to separate vascular districts, each anatomical atlas including a model for at least one vascular segment, branch or node within the corresponding vascular district; and a processor configured to execute the program instructions to:

collect IR data through the data entry fields within one or more of the data entry sheets, the IR data corresponding to a select IR procedure and a vascular district of interest;

obtain a candidate anatomical atlas from the multiple anatomical atlases stored in the memory based on the IR data collected, the candidate anatomical atlas including a model of at least one vascular segment, branch or node within the vascular district of interest and associated with the select IR procedure;

present for display the candidate anatomical atlas;

modify the candidate anatomical atlas based on user input;

generate a procedure-specific text reporting worksheet that includes statements based on the user input that modifies the candidate anatomical atlas;

create a patient-procedure-specific structured report based on the IR data collected, the patient-procedure-specific structured report including the procedure-specific text reporting worksheet and the candidate anatomical atlas as modified based on user input; and present for display the patient-procedure-specific structured report;

wherein the procedure-specific text reporting worksheet includes at least one of a) one or more text reporting regions that are uniquely associated with an associated candidate anatomical atlas, the text reporting region containing a narrative description of the select IR procedure, the narrative description comprising a plurality of standardized statements and b) a standardized statement for at least one of a condition, medical device or treatment associated with the select IR procedure, where the standardized statement is updated based on a user-specified modification to the candidate anatomical atlas.

2. The computer system of claim 1, wherein the memory stores the anatomical atlases in a library with the anatomical atlases corresponding to separate and distinct vascular districts, such anatomical atlases being created by the computer system in a configuration phase.

3. The computer system of claim 1, wherein at least a first anatomical atlas includes a vascular district model of vascular segments and a structural model of a portion of a human structural anatomy surrounding the vascular segments.

4. The computer system of claim 1, wherein the processor is configured to:

receive a condition or device designator indicating a point of interest in a vascular segment of the anatomical atlas, the condition designator indicative of a nature of a condition of the vascular segment, the device designator including a characteristic indicative of a device applied to the vascular segment at the point of interest; and superimpose a corresponding device or condition indicator on the vascular segment proximate to the point of interest, the condition indicator being indicative of the condition characteristic, the device indicator being indicative of the device applied to the vascular segment.

5. The computer system of claim 1, wherein the processor is configured to generate the procedure-specific text reporting worksheet by:
generating a procedure-specific worksheet that includes a text reporting region;
populating the text reporting region with a standardized statement for at least one of a condition, medical device or treatment associated with the select IR procedure;
receiving user input corresponding to a modification to at least one of the candidate anatomical atlas and the text reporting region; and
updating the standardized statement based on the user input.

6. A computer system for providing interventional radiology (IR), the computer system comprising:
memory storing program instructions and sets of data entry sheets having a predetermined format and data entry fields uniquely associated with a corresponding aspect of an IR procedure, and the memory further storing multiple anatomical atlases that correspond to separate vascular districts, each anatomical atlas including a model for at least one vascular segment, branch or node within the corresponding vascular district; and
a processor configured to execute the program instructions to:
collect IR data through the data entry fields within one or more of the data entry sheets, the IR data corresponding to a select IR procedure and a vascular district of interest;
obtain a candidate anatomical atlas from the multiple anatomical atlases stored in the memory based on the IR data collected, the candidate anatomical atlas including a model of at least one vascular segment, branch or node within the vascular district of interest and associated with the select IR procedure;
generate a text-based procedure-specific worksheet that includes a standardized statement for at least one of a condition, medical device or treatment associated with the candidate anatomical atlas;
modify the standardized statement based on a user-specified modification to the candidate anatomical atlas;
create a patient-procedure-specific structured report based on the IR data collected, the patient-procedure-specific structured report including the candidate anatomical atlas and the standardized statement as modified; and
present for display the patient-procedure-specific structured report.

7. A computer implemented method for providing interventional radiology (IR), the method comprising:
storing, in memory, program instructions and sets of data entry sheets having a predetermined format and data entry fields uniquely associated with a corresponding aspect of an IR procedure;
storing, in memory, multiple anatomical atlases that correspond to separate vascular districts, each anatomical atlas including a model for at least one vascular segment, branch or node within the corresponding vascular district; and displaying, in a graphical user interface (GUI), at least one data entry sheet that includes data entry fields;
collecting IR data, utilizing the GUI, through the data entry fields within the at least one data entry sheet, the IR data corresponding to a select IR procedure and a vascular district of interest;
obtaining a candidate anatomical atlas from the multiple anatomical atlases stored in the memory based on the IR data collected, the candidate anatomical atlas including a model of at least one vascular segment, branch or node within the vascular district of interest and associated with the select IR procedure;
creating a patient-procedure-specific structured report based on the IR data collected, the patient-procedure-specific structured report including the candidate anatomical atlas;
displaying in the GUI the patient-procedure-specific structured report including the candidate anatomical atlas; and
modifying the candidate anatomical atlas of the displayed patient-procedure-specific structured report based on user input, and displaying in the GUI the resultant anatomical atlas;
wherein the patient-procedure-specific structured report includes a text-based procedure-specific worksheet that includes one or more text reporting regions that are uniquely associated with candidate anatomical atlas, the text reporting region containing a narrative description of the select IR procedure, and the narrative description comprising a plurality of standardized statements.

8. The method of claim 7, further comprising:
storing the anatomical atlases in a library with the anatomical atlases corresponding to separate and distinct vascular districts.

9. The method of claim 7, wherein at least a first anatomical atlas includes a vascular district model of vascular segments and a structural model of a portion of a human structural anatomy surrounding the vascular segments.

10. The method of claim 7, further comprising:
receiving a condition designator indicating a point of interest in a vascular segment of the anatomical atlas, the condition designator indicative of a nature of a condition of the vascular segment; and
superimposing a condition indicator on the vascular segment proximate to the point of interest, the condition indicator being indicative of the condition characteristic.

11. The method of claim 7, wherein the condition designator corresponds to at least one of a stenosis or aneurysm.

12. The method of claim 7, further comprising:
receiving a device designator indicating a point of interest in a vascular segment of the anatomical atlas, the device designator including a characteristic indicative of a device applied to the vascular segment at the point of interest; and
superimposing a device indicator on the vascular segment at the point of interest, the device indicator being indicative of the device applied to the vascular segment.

13. The method of claim 7, wherein
the text-based procedure-specific worksheet includes a standardized statement for at least one of a condition, medical device or treatment associated with the select IR procedure, which is updated based on a user-specified modification to the candidate anatomical atlas.

14. The method of claim 13, wherein the text-based procedure-specific worksheet is generated by:
   populating a text reporting region of the text-based procedure-specific worksheet with a standardized statement for at least one of a condition, medical device or treatment;
   receiving user input corresponding to a modification to the candidate anatomical atlas; and
   updating the standardized statement based on the user input.

* * * * *